United States Patent
Kuo et al.

(10) Patent No.: US 10,870,702 B2
(45) Date of Patent: Dec. 22, 2020

(54) METHODS OF ASSESSING AND TREATING CANCER IN SUBJECTS HAVING DYSREGULATED LYMPHATIC SYSTEMS

(71) Applicant: Ensemble Group Holdings, Scottsdale, AZ (US)

(72) Inventors: Michael David Kuo, Scottsdale, AZ (US); Ching-Yu Huang, Scottsdale, AZ (US)

(73) Assignee: ENSEMLBLE GROUP HOLDINGS, Scottsdale, AZ (US)

( * ) Notice: Subject to any disclaimer, the term of this patent is extended or adjusted under 35 U.S.C. 154(b) by 0 days.

(21) Appl. No.: 16/155,726

(22) Filed: Oct. 9, 2018

(65) Prior Publication Data

US 2019/0040139 A1    Feb. 7, 2019

Related U.S. Application Data

(63) Continuation of application No. PCT/US2017/053504, filed on Sep. 26, 2017.

(60) Provisional application No. 62/412,488, filed on Oct. 25, 2016, provisional application No. 62/399,766, filed on Sep. 26, 2016.

(51) Int. Cl.

| | |
|---|---|
| C07K 16/28 | (2006.01) |
| C07K 16/22 | (2006.01) |
| A61P 35/00 | (2006.01) |
| A61B 5/055 | (2006.01) |
| A61B 5/00 | (2006.01) |
| A61B 6/03 | (2006.01) |
| A61K 31/4375 | (2006.01) |
| A61K 39/00 | (2006.01) |

(52) U.S. Cl.
CPC .......... *C07K 16/2818* (2013.01); *A61B 5/055* (2013.01); *A61B 5/418* (2013.01); *A61B 6/032* (2013.01); *A61B 6/037* (2013.01); *A61K 31/4375* (2013.01); *A61P 35/00* (2018.01); *C07K 16/22* (2013.01); *A61K 2039/505* (2013.01); *A61K 2039/507* (2013.01); *A61K 2039/545* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,092,885 A | 3/1992 | Yamada | |
| 5,112,946 A | 5/1992 | Maione | |
| 5,192,744 A | 3/1993 | Bouck | |
| 5,202,352 A | 4/1993 | Okada | |
| 6,395,718 B1 | 5/2002 | Slusher | |
| 6,462,075 B1 | 10/2002 | Bowen | |
| 6,465,431 B1 | 10/2002 | Thorn | |
| 6,475,784 B1 | 11/2002 | Papkoff | |
| 6,482,802 B1 | 11/2002 | Hu | |
| 6,482,810 B1 | 11/2002 | Brem | |
| 6,500,431 B1 | 12/2002 | Gill | |
| 6,500,924 B1 | 12/2002 | Brooks | |
| 6,518,298 B2 | 2/2003 | Green | |
| 6,521,439 B2 | 2/2003 | Folkman | |
| 6,525,019 B2 | 2/2003 | D Amato | |
| 6,538,103 B1 | 3/2003 | Ji | |
| 6,544,758 B2 | 4/2003 | O'Reilly | |
| 6,544,947 B2 | 4/2003 | Holaday | |
| 6,548,477 B1 | 4/2003 | Olson | |
| 6,559,126 B2 | 5/2003 | Tournaire | |
| 6,569,845 B1 | 5/2003 | Futamura | |
| 6,573,256 B2 | 6/2003 | Bishop | |
| 2012/0183547 A1 | 7/2012 | Skobe | |
| 2014/0193424 A1 | 7/2014 | Luo | |
| 2015/0210769 A1* | 7/2015 | Freeman | C07K 16/2896 424/136.1 |
| 2015/0225377 A1* | 8/2015 | Foitzik | A61K 31/337 514/210.2 |

FOREIGN PATENT DOCUMENTS

| | | |
|---|---|---|
| WO | 2015088847 | 6/2015 |
| WO | 2016069727 | 5/2016 |

OTHER PUBLICATIONS

Pitt et al (I, 44:1255-1269, 2016).*
Lloyd et al (Protein Engineering, Design & Selection, 22:159-168, 2009).*
Edwards et al (J Mol Biol, 14;334(1):103-118, 2003).*
[Fundamental Immunology p. 242 (William E. Paul, M.D. ed., 3d ed; 1993)].*
Stancovski et al (PNAS, 88: 8691-8695, 1991).*
Jiang et al. (J. Biol. Chem. Feb. 11, 2005; 280 (6): 4656-4662).*
Simon, Stacy (https://www.cancer.org/latest-news/fda-approves-keytruda-pembrolizumab-for-lung-cancer.html, accessed Apr. 9, 2020, pp. 1-2, 2015).*
Saif et al (JCO, 33(15): p. 3530, 2015).*
Kilvaer et al (PLoS ONE, 10(8):e0132481, pp. 1-17, 2015).*

(Continued)

*Primary Examiner* — Brad Duffy
(74) *Attorney, Agent, or Firm* — Dennis A. Bennett; Clifford Adam Schlecht; Charles H. Rexer, Jr.

(57) ABSTRACT

Provided herein is a method for determining cancer treatment using an immune modulating therapy in a subject in need thereof. The method comprises assessing whether a lymphatic system in a subject is dysregulated. When the lymphatic system is dysregulated, a treatment for the lymphatic system is determined before a therapeutic amount of an immune modulating therapy is administered to treat cancer in the subject. Alternatively, when the lymphatic system is dysregulated, an immune modulating therapy is selected to treat cancer in the subject, which immune modulating therapy is independent of immune-cell priming, antigen trafficking, antigen presentation, and any combination thereof. The subject may also be treated for cancer accordingly.

8 Claims, 7 Drawing Sheets

(56) References Cited

OTHER PUBLICATIONS

Alitalo, K. & Carmeliet, P. Molecular mechanisms of lymphangiogenesis in health and disease. Cancer Cell 1, 2002, pp. 219-227.

Blood, C. et al., "Tumor Interactions with the Vasculature: Angiogenesis and Tumor Metastasis", Bioch Biophys Acta., 1032(1):89-118, (1990).

Brakenhielm E. et al., Modulating metastasis by a lymphangiogenic switch in prostate cancer, Int J Cancer 121, 2153-61 (2007).

Bruce et al., Lymphangitis carcinomatosa: a literature review, J R Coll Surg Edinb 41:7-13 (1996).

Burton et al., Suppression of prostate cancer nodal and systemic metastasis by blockade of the lymphangiogenic axis Cancer Res 68, 7828-37 (2008).

Chen et al., Down-regulation of vascular endothelial cell growth factor-C expression using small interfering RNA vectors in mammary tumors inhibits tumor lymphangiogenesis and spontaneous metastasis and enhances survival, cancer Res 65, 9004-11 (2005).

Das. et al., "Vascular Endothelial Growth Factor-C Induces Lymphangitic Carcinomatosis, an Extremely Aggresive Form of Lung Metastases", Microenvironment and Immunology, Mar. 1, 2010, 12 pages.

Dieterich, et al., "Tumor-associated lymphatic Vessels Upregulate PDI1 to inhibit T-cell activation", Frontiers in Immunology, Feb. 2017, vol. 8, Article 66, pp. 1-13.

Fidler EJ., The pathogenesis of cancer metastasis: the 'seed and soil' hypothesis revisited, Nat Rev Cancer 3:453-8, (2003).

Frankhauser, et al., "Tumor lymphangiogenesis promotes T cell infiltration and potentiates immunotheraphy in melanoma", Science Translational Medicine, Sep. 13, 2017, 13 pages.

Garcia-Teijido P. et al., Tumor-Infiltrating Lymphocytes in Triple Negative Breast Cancer: The Future of Immune Targeting, Clin Med Insights Oncol. Apr. 5, 2016;10(Suppl 1): pp. 31-39.

Goldsmith et al., Pulmonary lymphangitic metastases from breast carcinoma, Arch Surg 94:483-8 (1967).

Ingber et al., Inhibition of angiogenesis through modulation of collagen metabolism, Lab. Invest. 59:44-51 (1988).

Janower et al., Lymphangitic spread of metastatic cancer to the lung. A radiologic-pathologic classification, Radiology 101:267-73 (1971).

Jeltsch et al., Hyperplasia of lymphatic vessels in VEGF-C transgenic mice, Science 276, 1423-5 (1997).

Joukov et al., A novel vascular endothelial growth factor, VEGF-C, is a ligand for the Flt4 (VEGFR-3) and KDR (VEGFR-2) receptor tyrosine kinases, EMBO J 15, 290-98 (1996).

Kawakami et al., Vascular endothelial growth factor C promotes lymph node metastasis in a rectal cancer orthotopic model, Surg Today 35, 131-8 (2005).

Kimura, et al., "Lymphatic dysfunction attenuates tumor immunity through impaired antigen presentation", www.impactjournals.com/oncotarget/, May 27, 2015, vol. 6, No. 20, pp. 18081-18093.

Krishnan et al., Differential in vivo and in vitro expression of vascular endothelial growth factor (VEGF)-C and VEGF-D in tumors and its relationship to lymphatic metastasis in immunocompetent rats, Cancer Res 63, 713-22 (2003).

Lee et al., Vascular endothelial growth factor-related protein: a ligand and specific activator of the tyrosine kinase receptor Flt4, Proc Natl Acad Sci USA 93, 1988-92 (1996).

Li H et al., Addition of bevacizumab enhances antitumor activity of erlotinib against non-small cell lung cancer xenografts depending on VEGF expression, Cancer Chemother Pharmacol. Dec. 2014;74(6): pp. 1297-1305.

Lin et al.,Inhibition of lymphogenous metastasis using adeno-associated virus-mediated gene transfer of a soluble VEGFR-3 decoy receptor, Cancer Res 65, 6901-9 (2005).

Lund, A. et al., "Lymphatic vessels regulate immune microenvironments in human and murine melanoma", The Journal of Clinical Investigation, Sep. 26, 2016, vol. 126, No. 9, pp. 3389-3402.

Lund, A. et al., "VEGF-C Promotes Immune Tolerance in B16 Melanomas and Cross-Presentation of Tumor Antigen by Lymph Node Lymphatic", Cell Reports, Mar. 29, 2012, pp. 191-199.

Mandriota, S. et al., "Vascular Endothelial Growth Factor-C-Mediated Lymphangiogenesis Promotes Tumour Metastasis", EMBO J., 20(4):672-82, (2001).

Mattila, M. et al., "VEGF-C Induced Lymphangiogenesis is Associated with Lymph Node Metastasis in Orthotopic MCF-7 Tumors", Int J Cancer, 98(6):946-51, (2002).

Moses, M. et al., "Identification of an Inhibitor of Neovascularization From Cartilage", Science, 248(4961):1408-10, (1990).

Nguyen, D. et al., "Metastasis: From Dissemination to Organ-Specific Colonization", Nat Rev Cancer, 9(4):274-84, (2009).

Pepper, M. et al., "Lymphatic Endothelium: Morphological, Molecular and Functional Properties", J Cell Biol., 163(2):209-13, (2003).

Petrova, T. et al., "VEGFR-3 Expression is Restricted to Blood and Lymphatic Vessels in Solid Tumors", Cancer Cell, 13(6):554-6, (2008).

Roberts, N. et al., "Inhibition of VEGFR-3 Activation with the Antagonistic Antibody More Potently Suppresses Lymph Node and Distant Metastases Than Inactivation of VEGFR-2", Cancer Res, 66(5):2650-7, (2006).

Skobe, M. et al., "Concurrent Induction of Lymphangiogenesis, Angiogenesis, and Macrophage Recruitment by Vascular Endothelial Growth Factor-C in Melanoma", Am J Pathol., 159(3):893-903, (2001).

Skobe, M. et al., "Induction of Tumor Lymphangiogenesis by VEGF-C Promotes Breast Cancer Metastasis", Nature Med, 7(2):192-8, (2001).

Smith, N. et al., "Vascular Endothelial Growth Factor Receptors VEGFR-2 and VEGFR-3 Are Localized Rrimarily to the Vasculature in Human Primary Solid Cancers", Clin Cancer Res., 16(14):3548-61, (2010).

Thomas, A. et al., "Pulmonary Lymphangitic Carcinomatosis as a Primary Manifestation of Colon Cancer in a Young Adult", CMAJ, 179(4):338-40, (2008).

Tomashefski and Dail, Dail and Hammar's Pulmonary Pathology (2008).

Valtola, R. et al., "VEGFR-3 and its Ligand VEGF-C are Associated with Angiogenesis in Breast Cancer", Am J Pathol, 154(5):1381-90, (1999).

Yanai, Y. et al., "Vascular Endothelial Growth Factor C Promotes Human Gastric Carcinoma Lymph Node Metastasi in Mice", J Exp Clin Cancer Res, 20(3):419-28, (2001).

Yang, Y. et al., "Fucoidan Inhibits Lymphangiogenesis by Downregulating the Expression of VEGFR3 and PROX1 in Human Lymphatic Endothelial Cells", Oncotarget, 7(25):38025-35, (2016).

Zhang, J. et al., "Targeting Cancer with Small Molecule Kinase Inhibitors", Nat Rev Cancer, 9(1):28-39, (2009).

Achen, M. et al., "Molecular Control of Lymphatic Metastasis", Ann NY Acad Sci., 1131:225-34, (2008).

Opthea, "Wet AMD and DME Therapies", 2019. https://www.opthea.com/, accessed Jul. 14, 2019.

Persaud, K. et al., "Involvement of the VEGF Receptor 3 in Tubular Morphogenesis Demonstrated with a Human Anti-Human VEGFR-3 Monoclonal Antibody that Antagonizes Receptor Activation by VEGF-C", J Cell Sci., 117(Pt 13):2745-56, (2004).

Sleeman, J. et al., "Tumor Metastasis and the Lymphatic Vasculature", Int J Cancer, 125(12):2747-56, (2009).

The ASCO Post, "VGX-100 Investigational New Drug Application Approved", Nov. 15, 2011. https://www.ascopost.com/issues/november-15/2011/vgx-100-investigational-new-drug-application-approved/, accessed Jul. 14, 2019.

International Application No. PCT/US2017/053504; International Preliminary Report on Patentability, dated Mar. 26, 2019; 10 pages.

Hemmila, I. et al., "Europium as a Label in Time-Resolved Immunofluorometric Assays", Anal Biochem., 137(2):335-43, (1984).

Ladner, R., "Mapping the epitopes of antibodies", Biotechnol Genet Eng Rev., 24:1-30, (2007).

Lövgren, T. et al., Collins, W (Ed.) "Alternative Immunoassays", John Wiley & Sons Ltd., pp. 203-217, (1985).

Mukkala, V. et al., "The Synthesis and Use of Activated N-benzyl Derivatives of Diethylenetriaminetetraacetic Acids: Alternative Reagents for Labeling of Antibodies with Metal Ions", Anal Biochem., 176(2):319-25, (1989).

(56) References Cited

OTHER PUBLICATIONS

Albiges, L. et al., "Efficacy of Targeted Therapies After PD-1/PD-L1 Blockade in Metastatic Renal Cell Carcinoma", Eur J Cancer, 51(17):2580-6, (2015).
Juneja, V. et al., "Enhancing the Efficacy of Checkpoint Blockade Through Combination Therapies", In: "Novel Immunotherapeutic Approaches to the Treatment of Cancer", pp. 1-39, (2016).
Kimura, T. et al., "Lymphatic Dysfunction Attenuates Tumor Immunity Through Impaired Antigen Presentation", Oncotarget, 6(20):18081-93, (2015).
Lee, C. et al., "Novel Antibodies Targeting Immune Regulatory Checkpoints for Cancer Therapy", Br J Clin Pharmacol., 76(2):233-47, (2013).
Moeini, S. et al., "Synergistic Effect og Programmed Cell Death Protein 1 Blockade and Secondary Lymphoid Tissue Chemokine in the Induction of Anti-Tumor Immunity by a Therapeutic Cancer Vaccine", Arch Virol., 162(2):333-46, (2016).
Ott, P. et al., "Inhibition of Immune Checkpoints and Vascular Endothelial Growth Factor as Combination Therapy for Metastatic Melanoma: An Overview of Rationale, Preclinical Evidence, and Initial Clinical Data", Front Oncol., 5:202, 7 pages, (2015).
Pedersen, A. et al., "Treatment of Transplanted CT26 Tumour With Dendritic Cell Vaccine in Combination With Blockade of Vascular Endothelial Growth Factor Receptor 2 and CTLA-4", Cancer Lett., 235(2):229-38, (2006).
Sachdev, J. et al., "Phase 1/2a Study of Double Immune Suppression Blockade by Combining a CSF1R Inhibitor (Pexidartinib/PLX3397) With an Anti PD-1 Antibody (Pembrolizumab) to Treat Advanced Melanoma and Other Solid Tumors", Gynecologic Oncol., 141(Poster 353):147-8, (2016).
Voron, T. et al., "VEGF-A Modulates Expression of Inhibitory Checkpoints on CD8-F T Cells in Tumors", J Exper Med., 212(2):139-48, (2015).
Yasuda, S. et al., "Simultaneous Blockade of Programmed Death 1 and Vascular Endothelial Growth Factor Receptor 2 (VEGFR2) Induces Synergistic Anti-Tumor Effect in Vivo", Clin Exper Immunol., 172(3):500-6, (2013).

\* cited by examiner

METHODS OF ASSESSING AND TREATING CANCER IN SUBJECTS HAVING DYSREGULATED LYMPHATIC SYSTEMS

This application is a continuation application of PCT/US2017/053504, filed Sep. 26, 2017, published as WO 2018/058125 on Mar. 29, 2018, entitled "Methods of Assessing and Treating Cancer in Subjects Having Dysregulated Lymphatic Systems," which claims the benefit of priority of U.S. Provisional Application No. 62/412,488 entitled "Methods of Treating Cancer Subjects with Immune Modulating Therapies and Regulators of Lymphatic Biology," filed Oct. 25, 2016, and U.S. Provisional Application No. 62/399,766 entitled "Methods of Determining Treatment with Immune Modulating Therapies in Cancer Subjects," filed Sep. 26, 2016; and the disclosures of which are incorporated herein by reference in their entireties for all purposes.

This disclosure relates to the field of diagnosing and treating cancer, particularly cancer in subjects having dysregulated lymphatic systems to whom an immune modulating therapy is applied.

Patients who suffer from a dysregulated lymphatic system do not respond to immune modulating therapies, which depend on immune cell priming, antigen presentation or antigen trafficking. Patients with tumors treated with cancer immune modulating therapy do not respond. By not responding, patients specifically rapidly progress from their tumor with minimal to no response period. Similarly, such patients have extremely poor overall survival compared to their counterparts who do not have dysregulation, or dysfunction of their lymphatic system. Also, patients with lymphangitic carcinomatosis or lymphatic invasion do not respond to such cancer immune modulating therapies, for a lack of immune cell activation and immune cell priming. A mouse melanoma model has shown that transgenic animals born without lymphatics do not have local tumor immune infiltrates, specific CD8 T cells and antigen presenting and dendritic cells in the tumor sites.

Taken together, prior studies examining the effects of blocking VEGF-C and its receptors on tumor metastasis have examined the effects of different antagonists on preventing metastatic spread of the primary tumor. But these prior studies have not discussed the effects of such antagonists on progression of established distant metastases after removal of the primary tumor. What is critically needed in the art are compositions and methods for achieving the treatment of established metastatic disease in cases when primary tumors have been removed or are non-resectable.

The foregoing examples of the related art and limitations related therewith are intended to be illustrative and not exclusive. Other limitations of the related art will become apparent to those of skill in the art upon a reading of the specification and a study of the drawings.

The following embodiments and aspects thereof are described and illustrated in conjunction with compositions and methods, which are meant to be exemplary and illustrative, not limiting in scope. In various embodiments, one or more of the above-described problems have been reduced or eliminated, while other embodiments are directed to other improvements.

Provided herein is a method for treating cancer in a subject in need thereof. The method comprises, when a lymphatic system in a subject is dysregulated, administering to the subject a therapeutic amount of a drug to regulate the dysregulated lymphatic system, and administering to the subject a therapeutic amount of an immune modifying therapy. Alternatively, when the lymphatic system is dysregulated, a therapeutic amount of an immune modulating therapy is administered to the subject, which immune modulating therapy operates independent of immune-cell priming, antigen trafficking, antigen presentation, and any combination thereof.

Also, provided herein is a method for determining cancer treatment using an immune modulating therapy in a subject in need thereof. The method comprises assessing whether a lymphatic system in a subject is dysregulated. When the lymphatic system is dysregulated, a treatment for the lymphatic system is determined before a therapeutic amount of an immune modulating therapy is administered to treat cancer in the subject. Alternatively, when the lymphatic system is dysregulated, an immune modulating therapy is selected to treat cancer in the subject, which immune modulating therapy is independent of immune-cell priming, antigen trafficking, antigen presentation, and any combination thereof.

Additional embodiments and features are in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification and the drawings, which forms a part of this disclosure.

BRIEF DESCRIPTION OF THE DRAWINGS

The disclosure will be readily understood by the following detailed description in conjunction with the accompanying drawings, wherein like reference numerals designate like structural elements. The drawings provide exemplary embodiments or aspects of the disclosure and do not limit the scope of the disclosure.

DETAILED DESCRIPTION

I. Methods for Determining Cancer Treatment

Provided herein is a method for determining cancer treatment using an immune modulating therapy in a subject in need thereof. The method comprises assessing whether a lymphatic system in a subject is dysregulated. When the lymphatic system is dysregulated, a treatment for the lymphatic system is determined before a therapeutic amount of an immune modulating therapy is administered to treat cancer in the subject. Alternatively, when the lymphatic system is dysregulated, an immune modulating therapy is selected to treat cancer in the subject, which immune modulating therapy is independent of immune-cell priming, antigen trafficking, antigen presentation, and any combination thereof.

Figure 1:
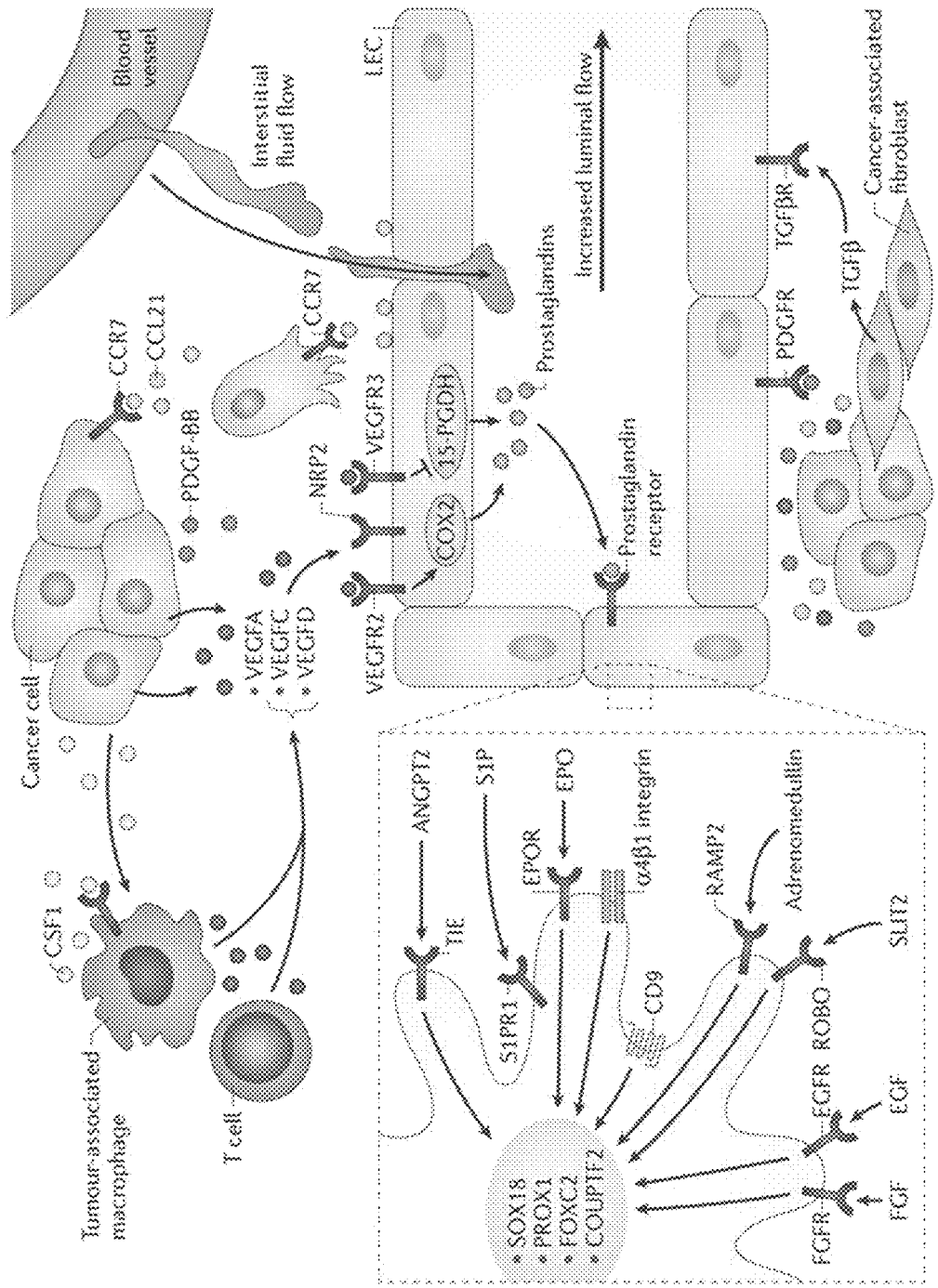
FIG. 1 is a schematic of general lymphatic biology showing molecules that modulate tumor lymphangiogenesis. See Stacker et al., "Lymphangiogenesis and lymphatic vessel remodeling in cancer," Nature Reviews Cancer, 14:159-172 (2014), incorporated herein by reference.

Molecules that modulate tumor lymphangiogenesis are shown at FIG. 1, with soluble ligands presented outside the cell, cognate receptors at the cell surface and transcription factors in the nucleus. Vascular endothelial growth factor C (VEGFC) and VEGFD refer to the proteolytically processed, biologically active forms of these proteins. Most ligands shown promote lymphangiogenesis, while transforming growth factor-β (TGFβ) inhibits lymphangiogenesis. Other molecules are known to participate in lymphatic development in the embryo, such as collagen and calcium binding EGF domain-containing protein 1 (CCBE1; not shown), for which a role in tumor lymphangiogenesis has not been shown. The interaction of tumor cells with lymphatic vessels can be promoted by interstitial fluid flow (which partly results from lymphatic drainage) via autologous chemotaxis involving chemokines, such as CC-chemokine ligand 21 (CCL21), and their receptors (CCR7 in the case of CCL21), expressed by tumor cells. Expression of CCL21 on lymphatic endothelial cells (LECs) can promote the entry of tumor cells into lymphatics via a CCR7-dependent mechanism. Producing lymphangiogenic growth factors, such as VEGFC and VEGFD, can drive the formation of new lymphatics and lymphatic enlargement near a tumor, which increases the surface area for the interaction of tumor cells with lymphatics. VEGFC can also promote tumor cell invasiveness in an autocrine manner, and it can upregulate the production of CCL21 on lymphatic vessels. The other abbreviations listed are 15-PGDH, 15-hydroxyprostaglandin dehydrogenase; ANGPT2, angiopoietin 2; COUPTF2, COUP transcription factor 2; COX2, cyclooxygenase 2; CSF1, colony-stimulating factor 1; EGF, epidermal growth factor; EGFR, EGF receptor; EPO, erythropoietin; EPOR, EPO receptor; FGF, fibroblast growth factor; FGFR, FGF receptor; FOXC2, forkhead box protein C2; PDGF-BB, platelet-derived growth factor BB; PDGFR, PDGF receptor; PROX1, prospero homeobox protein 1; RAMP2, receptor activity-modifying protein 2; S1P, sphingosine-1-phosphate; TGFβR, TGFβ receptor; VEGFR, VEGF receptor.

Figure 2:
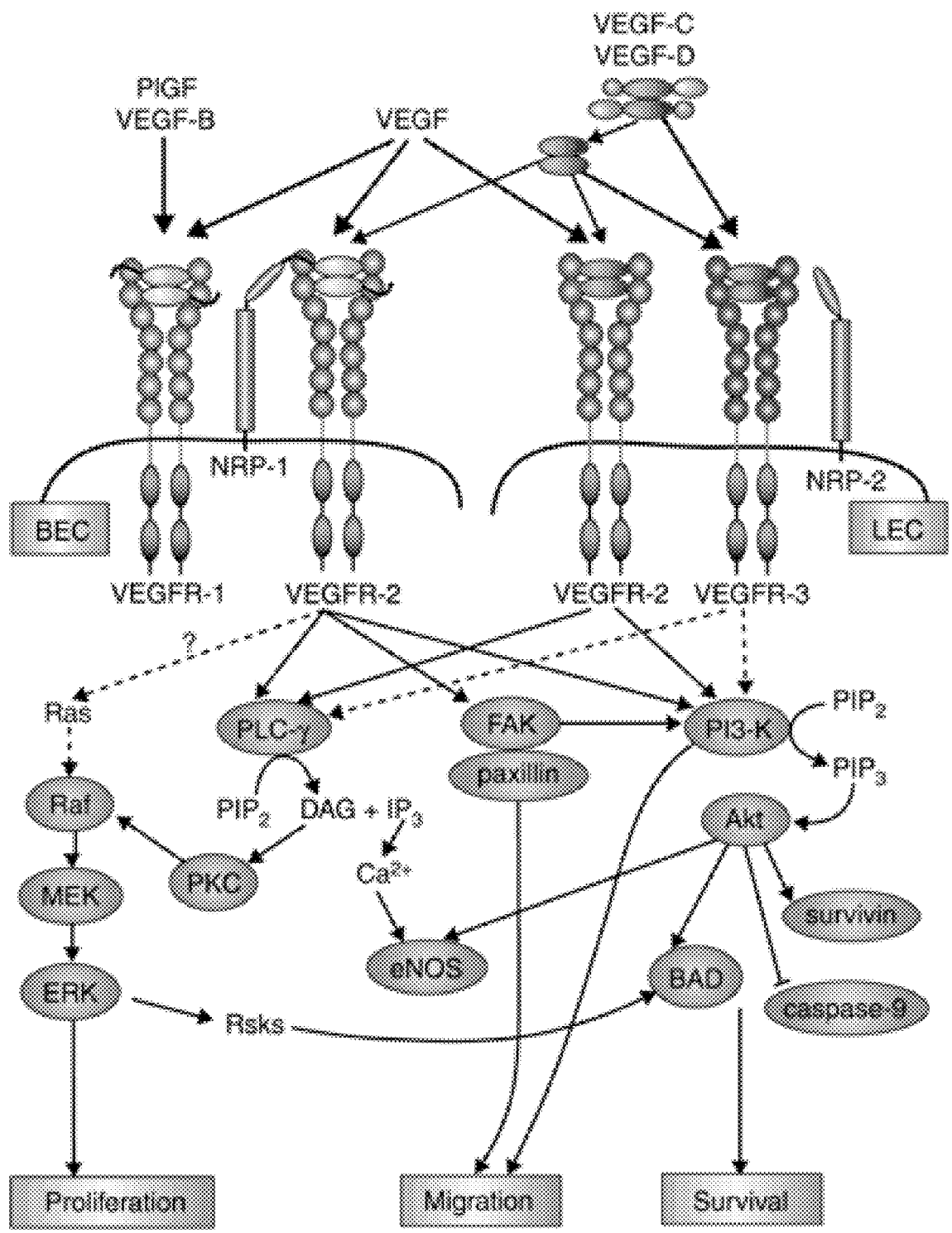
FIG. 2 is a schematic showing The VEGF family of ligands and their respective binding patterns to the VEGFR. See Karkkainen et al., "Lymphatic endothelium: a new frontier of metastasis research," Nature Cell Biology, 4:E2-E5 (2002).

The VEGF family of ligands and their respective binding patterns to the VEGFRs are shown at FIG. 2. VEGFR-1 and neuropilin-1 (NRP-1) are expressed in blood vascular ECs, VEGFR-3 and NRP-2 in lymphatic ECs, and VEGFR-2 occurs in both cell lineages. VEGFR-2 is the main signal transducing receptor, as it activates several downstream signaling molecules (circles), and induces responses such as cell proliferation, migration and survival. The protein kinase C (PKC)-mediated MEK/ERK pathway produces proliferation signals, in contrast to activating the PI3-kinase/Akt pathway, which regulates cell survival. Focal adhesion kinase (FAK) and PI3-kinase migrate cells by stimulating the reorganization of actin and recruitment of actin-anchoring proteins to the focal adhesions. VEGF-C and VEGF-D are ligands for VEGFR-3, and they can induce LEC survival, migration and growth via activation of the MEK/ERK and PI3-kinase/Akt pathways. However, after proteolytic cleavage, VEGF-C and VEGF-D can also bind and activate VEGFR-2 and stimulate both BECs and LECs. The distinct but overlapping receptor specificities and receptor expression patterns determine how VEGFs can differentially target both the blood vascular and/or lymphatic endothelium.

The lymphatic system may be assessed through imaging. The imaging may comprise one or more selected from the group consisting of computer-assisted tomography (CAT), magnetic resonance imaging (MRI), positron emission tomography (PET), lymphoscintigraphy, and radiography of radiolabeled agents. The imaging may be computer-assisted tomography (CAT). The imaging may be magnetic resonance imaging (MRI). The imaging may be positron emission tomography (PET). The imaging may be lymphoscintigraphy. The imaging may be radiography of radiolabeled agents.

The lymphatic system may be assessed by measuring levels in a tissue sample of one of more first factors selected from the group consisting of D2-40, podoplanin, CD34, and LYVE-1.

The first factor may be D2-40, a monoclonal antibody to an MW 40,000 O-linked sialoglycoprotein that reacts with a fixation-resistant epitope on lymphatic endothelium.

The first factor may be podoplanin.

The first factor may be CD34. Hematopoietic progenitor cell antigen CD34 also known as CD34 antigen is a protein that in humans is encoded by the CD34 gene. CD34 is a cluster of differentiation in a cell surface glycoprotein and functions as a cell-cell adhesion factor. CD34 may also mediate the attachment of stem cells to bone marrow extracellular matrix or directly to stromal cells.

The first factor may be LYVE-1. Lymphatic vessel endothelial hyaluronan receptor 1 (LYVE1), also known as extracellular link domain containing 1 (XLKD1) is a Link domain-containing hyaladherin, a protein capable of binding to hyaluronic acid (HA), homologous to CD44, the main HA receptor. In humans, it is encoded by the LYVE1 gene.

The tissue sample may be concurrently stained for one or more second factors selected from the group consisting of angiopoietin-1, angiopoietin-2, BMP-9, EGF, endoglin, endothelin-1, FGF-1, FGF-2, follistatin, G-CSF, HB-EGF, HGF, IGF, IL-8, leptin, MMP-2, MMP-9, NRP 1, NRP 2, PDGF, PIGF, PLGF, TIE1/2, VEGF-A, VEGF-C, and VEGF-D to determine levels of these factors within lymphatics.

The second factor may be angiopoietin-1. The second factor may be angiopoietin-2.

The second factor may be BMP-9, also known as GDF2, contains an N-terminal TGF-beta-like pro-peptide (prodomain) (residues 56-257) and a C-terminal transforming growth factor beta superfamily domain (325-428). GDF2 (BMP9) is secreted as a pro-complex consisting of the BMP9 growth factor dimer non-covalently bound to two BMP9 prodomain molecules in an open-armed conformation.

The second factor may be epidermal growth factor (EGF), which stimulates cell growth and differentiation by binding to its receptor, EGFR. Human EGF is a 6-kDa protein with 53 amino acid residues and three intramolecular disulfide bonds.

The second factor may be endoglin (ENG), which is a type I membrane glycoprotein on cell surfaces and is part of the TGF beta receptor complex. Endoglin is also commonly referred to as CD105, END, FLJ41744, HHT1, ORW and ORW1. Endoglin has a crucial role in angiogenesis, therefore, making it an important protein for tumor growth, survival and metastasis of cancer cells to other locations in the body.

The second factor may be endothelin-1 (ET-1), also known as preproendothelin-1 (PPET1), is a potent vasoconstrictor that in humans is encoded by the EDN1 gene and produced by vascular endothelial cells. The protein encoded by this gene is proteolytically processed to release a secreted peptide termed endothelin 1. Endothelin 1 is one of three isoforms of human endothelin.

The second factor may be heparin-binding growth factor 1 (FGF-1) is a protein that in humans is encoded by the FGF1 gene.

The second factor may be heparin-binding growth factor 2 (FGF-2) is a protein that in humans is encoded by the FGF2 gene. FGF-1.

The second factor may be follistatin, also known as "activin-binding protein." Folliostatin is a protein that in humans is encoded by the FST gene. Follistatin is an autocrine glycoprotein expressed in all tissues of higher animals.

The second factor may be granulocyte-colony stimulating factor (G-CSF or GCSF), also known as colony-stimulating factor 3 (CSF 3). G-CSF is a glycoprotein that stimulates the bone marrow to produce granulocytes and stem cells and release them into the bloodstream. Functionally, it is a cytokine and hormone, a type of colony-stimulating factor, and is produced by many different tissues. The pharmaceutical analogs of naturally occurring G-CSF are called filgrastim and lenograstim. G-CSF also stimulates the survival, proliferation, differentiation, and function of neutrophil precursors and mature neutrophils.

The second factor may be heparin-binding EGF-like growth factor (HB-EGF), which is a member of the EGF family of proteins that in humans is encoded by the HBEGF gene. HB-EGF-like growth factor is synthesized as a membrane-anchored mitogenic and chemotactic glycoprotein. An epidermal growth factor produced by monocytes and macrophages, due to an affinity for heparin is termed HB-EGF. It plays a role in wound healing, cardiac hypertrophy, and heart development and function. HB-EGF is an 87-amino acid glycoprotein that displays highly regulated gene expression. Ectodomain shedding results in the soluble mature form of HB-EGF, which influences the mitogenicity and chemotactic factors for smooth muscle cells and fibroblasts. The transmembrane form of HB-EGF is the unique receptor for diphtheria toxin and functions in juxtracrine signaling in cells. Both forms of HB-EGF participate in normal physiological processes and in pathological processes including tumor progression and metastasis, organ hyperplasia, and atherosclerotic disease. HB-EGF can bind two locations on cell surfaces: heparan sulfate proteoglycans and EGF-receptor effecting cell to cell interactions.

The second factor may be hepatocyte growth factor (HGF) or scatter factor (SF). HGF is a paracrine cellular growth, motility and morphogenic factor. HGF is secreted by mesenchymal cells and targets and acts primarily upon epithelial cells and endothelial cells, but also acts on haemopoietic progenitor cells and T cells. It has a major role in embryonic organ development, specifically in myogenesis, in adult organ regeneration, and in wound healing.

The second factor may be insulin-like growth factor 1 (IGF-1), also called somatomedin C. IFG-1 is a protein that in humans is encoded by the IGF1 gene. IGF-1 has also been referred to as a "sulfation factor" and its effects were termed "nonsuppressible insulin-like activity" (NSILA).

The second factor may be interleukin 8 (IL-8 or chemokine (C-X-C motif) ligand 8, CXCL8) is a chemokine produced by macrophages and other cell types such as epithelial cells, airway smooth muscle cells and endothelial cells. Endothelial cells store IL-8 in their storage vesicles, the Weibel-Palade bodies. In humans, the interleukin-8 protein is encoded by the CXCL8 gene. IL-8 is initially produced as a precursor peptide of 99 amino acids which then undergoes cleavage to create several active IL-8 isoforms. In culture, a 72-amino acid peptide is the major form secreted by macrophages.

The second factor may be leptin. Leptin the "satiety hormone", is a hormone made by adipose cells that helps to regulate energy balance by inhibiting hunger. Leptin is opposed by the actions of the hormone ghrelin, the "hunger hormone". Both hormones act on receptors in the arcuate nucleus of the hypothalamus to regulate appetite to achieve energy homeostasis. In obesity, a decreased sensitivity to leptin occurs, resulting in an inability to detect satiety despite high energy stores.

The second factor may be matrix metalloproteinase 2 (MMP-2). Also known as 72 kDa type IV collagenase and gelatinase A, MMP-2 is an enzyme that in humans is encoded by the MMP2 gene. The MMP2 gene is on chromosome 16 at position 12.2.

The second factor may be matrix metalloproteinase 9 (MMP-9). Also known as 92 kDa type IV collagenase, 92 kDa gelatinase or gelatinase B (GELB), MMP-9 is a matrixin, a class of enzymes that belong to the zinc-metalloproteinases family involved in the degradation of the extracellular matrix. In humans, the MMP9 gene encodes for a signal peptide, a propeptide, a catalytic domain with inserted three repeats of fibronectin type II domain followed by a C-terminal hemopexin-like domain.

The second factor may be neuropilin-1 (NRP-1) is a protein that in humans is encoded by the NRP1 gene. In humans, the neuropilin 1 gene is at 10p11.22.

The second factor may be neuropilin-2 (NRP-2). NRP-2 is a protein that in humans is encoded by the NRP2 gene. This gene encodes a member of the neuropilin family of receptor proteins. The encoded transmembrane protein binds to SEMA3C protein {sema domain, immunoglobulin domain (Ig), short basic domain, secreted, (semaphorin) 3C} and SEMA3F protein {sema domain, immunoglobulin domain (Ig), short basic domain, secreted, (semaphorin) 3F}, and interacts with vascular endothelial growth factor (VEGF). This protein may play a role in cardiovascular development, axon guidance, and tumorigenesis. Multiple transcript variants encoding distinct isoforms have been identified for this gene.

The second factor may be platelet-derived growth factor (PDGF) is one of many growth factors that regulate cell growth and division. PDGF plays a significant role in blood vessel formation (angiogenesis), the growth of blood vessels from already-existing blood vessel tissue, mitogenesis, i.e. proliferation, of mesenchymal cells such as fibroblasts, osteoblasts, tenocytes, vascular smooth muscle cells and mesenchymal stem cells as well as chemotaxis, the directed migration, of mesenchymal cells. Platelet-derived growth factor is a dimeric glycoprotein that can be composed of two A subunits (PDGF-AA), two B subunits (PDGF-BB), or one of each (PDGF-AB).

The second factor may be phosphatidylinositol-glycan biosynthesis class F protein (PIGF).

The second factor may be placental growth factor (PGF), a protein that in humans is encoded by the PGF gene. PGF is a member of the VEGF (vascular endothelial growth factor) sub-family. The main source of PGF during pregnancy is the placental trophoblast. PGF is also expressed in many other tissues, including the villous trophoblast.

The second factor may be tyrosine kinase with immunoglobulin-like and EGF-like domains 1 and 2 (TIE1/2), which is an angiopoietin receptor which in humans is encoded by the TIE1 gene.

The second factor may be vascular endothelial growth factor A (VEGF-A). The second factor may be vascular endothelial growth factor C (VEGF-C). The second factor may be vascular endothelial growth factor D (VEGF-D).

The lymphatic system may be assessed from elevated levels measured using a flow-cytometry-based multiplex assay or an enzyme-linked immunosorbent assay. The lymphatic system may be assessed from elevated levels measured using a flow-cytometry-based multiplex assay. The lymphatic system may be assessed from elevated levels measured using an enzyme-linked immunosorbent assay.

The lymphatic system may be assessed from expression levels measured by one or more techniques selected from the group consisting of immunohistochemistry, gene expression profiling, and polymerase chain reaction (PCR)-based cDNA amplification of a lymphangiogenesis-regulating gene. The lymphatic system may be assessed from expression levels measured by immunohistochemistry. The lymphatic system may be assessed from expression levels measured by gene expression profiling. The lymphatic system may be assessed from expression levels measured by polymerase chain reaction (PCR)-based cDNA amplification of a lymphangiogenesis-regulating gene.

The lymphangiogenesis-regulating gene may be one or more selected from the group selected from angiopoietin-1, angiopoietin-2, BMP-9, EGF, endoglin, endothelin-1, FGF-1, FGF-2, follistatin, G-CSF, HB-EGF, HGF, IGF, IL-8, leptin, MMP-2, MMP-9, NRP 1, NRP 2, PDGF, PIGF, PLGF, TIE1/2, VEGF-A, VEGF-C, and VEGF-D. The lymphangiogenesis-regulating gene may be angiopoietin-1. The lymphangiogenesis-regulating gene may be angiopoietin-2. The lymphangiogenesis-regulating gene may be BMP-9. The lymphangiogenesis-regulating gene may be EGF. The lymphangiogenesis-regulating gene may be endoglin. The lymphangiogenesis-regulating gene may be endothelin-1. The lymphangiogenesis-regulating gene may be FGF-1. The lymphangiogenesis-regulating gene may be FGF-2. The lymphangiogenesis-regulating gene may be follistatin. The lymphangiogenesis-regulating gene may be G-CSF. The lymphangiogenesis-regulating gene may be HB-EGF. The lymphangiogenesis-regulating gene may be HGF. The lymphangiogenesis-regulating gene may be IGF. The lymphangiogenesis-regulating gene may be IL-8. The lymphangiogenesis-regulating gene may be leptin. The lymphangiogenesis-regulating gene may be MMP-2. The lymphangiogenesis-regulating gene may be MMP-9. The lymphangiogenesis-regulating gene may be NRP 1. The lymphangiogenesis-regulating gene may be NRP 2. The lymphangiogenesis-regulating gene may be PDGF. The lymphangiogenesis-regulating gene may be PIGF. The lymphangiogenesis-regulating gene may be PLGF. The lymphangiogenesis-regulating gene may be TIE1/2. The lymphangiogenesis-regulating gene may be VEGF-A. The lymphangiogenesis-regulating gene may be VEGF-C. The lymphangiogenesis-regulating gene may be VEGF-D.

The lymphatic system may be assessed by profiling immune cells directly in a specimen by flow cytometry, mass spectrometry, cell labeling, or any combination thereof. The lymphatic system may be assessed by profiling immune cells directly in a specimen by flow cytometry. The lymphatic system may be assessed by profiling immune cells directly in a specimen by mass spectrometry. The lymphatic system may be assessed by profiling immune cells directly in a specimen cell labeling.

The lymphatic system may be assessed by measuring one or more markers selected from the group selected from angiopoietin-1, angiopoietin-2, heparin-binding factor midkine, BMP-9, EGF, endoglin, endothelin-1, FGF-1, FGF-2, follistatin, G-CSF, HB-EGF, HGF, IGF, IL-8, leptin, MMP-2, MMP-9, NRP 1, NRP 2, PDGF, PIGF, PLGF, TIE1/2, VEGF-A, VEGF-C, and VEGF-D. The marker may be angiopoietin-1. The marker may be angiopoietin-2. The marker may be heparin-binding factor midkine. The marker may be BMP-9. The marker may be EGF. The marker may be endoglin. The marker may be endothelin-1. The marker may be FGF-1. The marker may be FGF-2. The marker may be follistatin. The marker may be G-CSF. The marker may be HB-EGF. The marker may be HGF. The marker may be IGF. The marker may be IL-8. The marker may be leptin. The marker may be MMP-2. The marker may be MMP-9. The marker may be NRP 1. The marker may be NRP 2. The marker may be PDGF. The marker may be PIGF. The marker may be PLGF. The marker may be TIE1/2. The marker may be VEGF-A. The marker may be VEGF-C. The marker may be VEGF-D.

The art teaches that a patient's response to immune therapy depends on the PD-1 or PD-L1 expression or tumor neoantigen status. For examples, hypermutant, microsatellite instability-high, DNA mismatch repair deficient (dMMR), or high neoantigen burden phenotype tumors respond strongly to checkpoint immune therapies. The cancers which are low in or do not express PD-1 or PDL-1, or are not hypermutant, not dMMR, microsatellite instability-low or normal, or have low neoantigen burdens, do not respond to checkpoint immune therapy. Breast cancer, particularly triple negative (HER2−, ER−, PR−), ER+/HER2 negative, and inflammatory breast cancers, microsatellite instability low or normal, nonhypermutant/DNA mismatch repair low or normal colorectal cancers, and glioblastomas multiforme (GBMs), pancreatic cancer, sarcomas, and prostate cancers do not respond well to immune-modulating therapies. To the contrary, the present disclosure shows that the tumor types described above respond to immune checkpoint inhibition when treated in relation to lymphatic dysfunction, independent of PD-1/PD-L1, microsatellite instability degree, dMMR status, or neoantigen/hypermutant tumor status or type (see Example 4).

II. Methods for Treating Cancer

Also, provided herein is a method for treating cancer in a subject in need thereof. The method comprises, when a lymphatic system in a subject is dysregulated, administering to the subject a therapeutic amount of a drug to regulate the dysregulated lymphatic system, and administering to the subject a therapeutic amount of an immune modifying therapy. Alternatively, when the lymphatic system is dysregulated, a therapeutic amount of an immune modulating therapy is administered to the subject, which immune modulating therapy operates independent of immune-cell priming, antigen trafficking, antigen presentation, and any combination thereof.

The art suggests that tumors with high levels of lymphangiogenesis should have a better prognosis and better response to immune therapies because they have higher tumor immune cell infiltrates. To the contrary, following the present disclosure, such tumors should be treated with both immune modulation therapies, including immune checkpoint inhibitors, and a modulator of lymphatic biology, such as a VEGR-3 inhibitor, VEGF-C, VEGF-D, NRP 1, NRP 2, or CCPE1.

As such, therapies that modulate (stimulate or inhibit) immune biology at or downstream of this step are not effective monotherapies. They must be replaced with alternate therapies not dependent on these steps or mechanisms and treated with alternate therapies or these immune modulating therapies will either need to be independent of immune cell priming, antigen priming, or presentation or the immune modulating therapies that are dependent on these steps will need to be augmented or changed by agents that help to limit or overcome these issues. Further, cancer patients treated with immune modulating therapies dependent on immune cell priming, antigen trafficking or antigen presentation (e.g. immune checkpoint therapies) or patients that have dysregulated, dysfunctional or perturbed lymphatic systems can as a class all be augmented and their clinical profiles improved through augmentation with such agents (antibody or antibody derivatives, or small molecular or small molecule derativites) that regulate lymphatic angiogenesis.

Further, based on evaluation of the status of the lymphatic system in the cancer subject, the potential treatment with an immune-modulating therapy is assessed. If subjects are determined to have dysregulation of their lymphatic system by having abnormal lymphatic system features, then the treatment with any immune-modulating therapy that depends on efficient immune cell priming or antigen presentation is either aborted, deferred, or is augmented by a treatment method that modulates the lymphatic system to overcome or offset the dysfunctions.

Targeting lymphatics surrounding cancer therapy exclusively focuses on lymphatics as conduits for metastasis and as a means of limiting metastasis by preventing cancer cell spread along these conduits. The prior art focuses on these therapies in the context of providing more support around tumor associated blood vessel angiogenesis by covering the vascular angiogenesis pathway that existing and marketed do not cover. The art does not teach specific and highly selective inhibitors of lymphangiogenesis for augmenting or aiding immune modulation or immune therapies. The prior art also does not teach aiding immune checkpoint inhibitors as a principal means of augmenting the effects of these therapies, supporting or boosting immune therapies. Additionally, the prior art does not teach lymphangiogenesis inhibitors in combination with immune modulating therapies in patients with lymphatic dysregulation, dysfunction, or perturbation.

The prior art does not teach treating patients with dysfunctional, dysregulated or perturbed lymphatic systems as characterized by lymphatic invasion and or lymphangitic carcinomatosis. While the prior art suggested anti-lymphangiogenic agents in ongoing clinical trials, the agents were selected solely for their known role as primary cancer therapies that target and inhibit vascular angiogenesis and do not selectively inhibit lymphangiogenesis. They are nonspecific agents with high general specificity for the entire VEGF family of receptors and many other angiogenesis related targets (e.g. PDGF-BB, HGF, etc.), not specific and selective agents for VEGF-C/D and VEGFR 3. Additionally, the prior art does not teach lymphatic biology specific mediators as for treating dysregulated lymphatics in the singular role of cancer immunotherapy for targeting lymphatic dysregulation so that immune therapies can more effectively function.

In a clinical setting, a major challenge is treatment of established metastatic disease after the primary tumor has been surgically removed, eradicated by other means, or is unresectable. Following the present disclosure, established metastatic disease by blocking lymphangiogenesis using antagonists of VEGF-C receptors, VEGFR-3 and VEGFR-2 in combination with cancer immune modulating therapies which can include but are not limited to immune checkpoint inhibitors and in the setting of a dysregulated lymphatic system, or tumor associated lymphatic invasion, lymphangitic carcinomatosis, or impaired antigen presentation, immune cell activation or priming alone or due to an impaired or dysregulated, dysfunctional or perturbed lymphatic system.

Specifically, the present disclosure provides a method for inhibiting an established tumor metastasis in a subject comprising administering to said subject a therapeutically effective amount of one or more VEGFR-3 antagonist(s) and optionally one or more VEGFR-2 antagonist(s) with cancer immune modulating therapies which can include but are not limited to immune checkpoint inhibitors and in the setting of a dysregulated lymphatic system, or tumor associated lymphatic invasion, lymphangitic carcinomatosis, or impaired antigen presentation, immune cell activation or priming alone or due to an impaired or dysregulated, dysfunctional or perturbed lymphatic system. A method is provided for inhibiting lymphangiogenesis in a subject with a metastatic disease comprising administering to said subject a therapeutically effective amount of one or more VEGFR-3 antagonist(s) and optionally one or more VEGFR-2 antagonist(s) in combination with cancer immune modulating therapies which can include but are not limited to immune checkpoint inhibitors and in the setting of a dysregulated lymphatic system, or tumor associated lymphatic invasion, lymphangitic carcinomatosis, or impaired antigen presentation, immune cell activation or priming alone or due to an impaired or dysregulated, dysfunctional or perturbed lymphatic system.

A. Lymphatic system

The lymphatic system comprises capillaries and larger collecting vessels continuously lined by endothelial cells which return extravasated fluid and macromolecules from the interstitial space back to the blood circulation. Thus, the lymphatic system plays a vital role in the regulation of fluid, protein, and pressure equilibrium in tissues. By directing leukocytes and antigens from tissues to the lymph nodes, lymphatic vessels also have a key function in immune surveillance. Dysfunction of the lymphatic system results in lymphedema, a chronic and disabling condition for which there are no treatments now available. Breast cancer treatment is associated with lymphedema, which often develops following surgical removal of lymph nodes and radiation therapy.

The lung is a common site for metastasis of many tumors, including common tumors such as breast, colorectal, prostate, bronchial, head-and-neck, and renal cancers. Pulmonary nodules are the most common manifestation of metastatic cancer in the lungs. Without wishing to be bound by theory, they are thought to be derived from tumor emboli which arrest in the lung capillaries and invade into the surrounding lung tissue. Involvement of pulmonary lymphatic vessels with cancer is less diagnosed because of the imaging difficulties. At necropsy, metastases via pulmonary lymphatics and bronchial arteries are often seen.

Involving lung lymphatics with cancer is a hallmark of a very aggressive metastatic disease, designated "lymphangitic carcinomatosis." The prognosis for a patient with this clinical picture is extremely poor; 50% of the patients die within 3 months of diagnosis. Although lymphangitic spread can be caused by any malignant cancer, it most commonly results from tumors originating in the breast, stomach, pancreas, lung, or prostate. This phenomenon is also caused by primary pulmonary carcinoma, especially small cell carcinoma and adenocarcinoma. Because of the extremely aggressive nature of this disease, there is a great need for early diagnosis and treatment. Before the present disclosure, no treatment improved outcome of patients with lymphangitic carcinomatosis.

Lymphangitic carcinomatosis is an aggressive disease that has been seen in association with many common metastatic cancers such as breast, gastric, pancreatic, prostate cancer and others. Primary lung cancer can also present in the form of lymphangitic carcinomatosis, suggesting that targeting of VEGF-C/VEGFR-3 in lung cancer could be a treatment option for slowing the progression of lung cancer in combination with cancer immune modulating therapies which can include, but are not limited, to immune checkpoint inhibitors and in the setting of a dysregulated lymphatic system, or tumor associated lymphatic invasion, lymphangitic carcinomatosis, or impaired antigen presentation, immune cell activation or priming alone or due to an impaired or dysregulated, dysfunctional or perturbed lymphatic system.

Clinically, lymphangitic carcinomatosis is characterized by the presence of malignant cells in the lymphatic vessels localized in the peri-bronchovascular area, in the interlobular septa, and in the centrilobular region. Associated pleural involvement is common. Edema, resulting from blockage of lymphatic drainage and a desmoplastic reaction, are common and can contribute to interstitial thickening. Hilar and mediastinal lymphadenopathy are present in 20-40% of patients, and pleural effusions are present in 30-50% of patients.

The dysregulated lymphatic system may be characterized by one or more selected from the group consisting of abnormal lymphatic development, lymphatic proliferation, lymphangiogenesis, impaired lymphatic vessel function, dysregulated lymphatic vessel function, augmented tumor cell lymphatic infiltration, lymphangitic carcinomatosis, abnormal functioning or homeostatic regulation, lymphatic remodeling, physical pressure upon lymphatics, altered tumoral lymphatic development, altered tumoral lymphangiogenesis, and output blockage of lymphatic structures in lymphatic organs. The dysregulated lymphatic system may be characterized by abnormal lymphatic development. The dysregulated lymphatic system may be characterized by lymphatic proliferation. The dysregulated lymphatic system may be characterized by lymphangiogenesis. The dysregulated lymphatic system may be characterized by impaired lymphatic vessel function. The dysregulated lymphatic system may be characterized by dysregulated lymphatic vessel function. The dysregulated lymphatic system may be characterized by augmented tumor cell lymphatic infiltration. The dysregulated lymphatic system may be characterized by lymphangitic carcinomatosis. The dysregulated lymphatic system may be characterized by abnormal functioning or homeostatic regulation. The dysregulated lymphatic system may be characterized by lymphatic remodeling. The dysregulated lymphatic system may be characterized by physical pressure upon lymphatics. The dysregulated lymphatic system may be characterized by altered tumoral lymphatic development. The dysregulated lymphatic system may be characterized by altered tumoral lymphangiogenesis. The dysregulated lymphatic system may be characterized by output blockage of lymphatic structures in lymphatic organs.

B. Drug to Regulate the Lymphatic System

The drug to regulate the lymphatic system may be administered before the therapeutic amount of the immune modifying therapy.

The drug to regulate the lymphatic system may be administered concurrently with the therapeutic amount of the immune modifying therapy.

The drug to regulate the lymphatic system may be an inhibitor or an antagonist for a target selected from the group consisting of (1) inhibitors and antagonists of VEGFR-2, heparin-binding factor midkine, VEGFR-3, VEGF-C, VEGF-D, Ang2/Tie2, NRP 1, NRP 2, CCPE1, CSF1, CSFR1, and CCL21; (2) a regulator of lymphatic endothelial cell metabolism; (3) an enzyme involved in lymphatic endothelial cell fatty acid oxidation; (4) a regulator of PROX1; and any combination thereof.

The drug to regulate the lymphatic system may inhibit VEGFR-2. The drug to regulate the lymphatic system may antagonize VEGFR-2. The drug to regulate the lymphatic system may inhibit VEGFR-3. The drug to regulate the lymphatic system may antagonize VEGFR-3. The drug to regulate the lymphatic system may inhibit VEGF-C. The drug to regulate the lymphatic system may antagonize VEGF-C. The drug to regulate the lymphatic system may inhibit VEGF-D. The drug to regulate the lymphatic system may antagonize VEGF-D. The drug to regulate the lymphatic system may inhibit Ang2/Tie2. The drug to regulate the lymphatic system may antagonize Ang2/Tie2. The drug to regulate the lymphatic system may inhibit NRP 1. The drug to regulate the lymphatic system may antagonize NRP 1. The drug to regulate the lymphatic system may inhibit NRP 2. The drug to regulate the lymphatic system may antagonize NRP 2. The drug to regulate the lymphatic system may inhibit a CCPE1. The drug to antagonize the lymphatic system may be a CCPE1.

The drug to regulate the lymphatic system may inhibit colony stimulating factor 1 (CSF1). The drug to regulate the lymphatic system may antagonize CSF1. Also known as macrophage colony-stimulating factor (M-CSF), is a secreted cytokine which influences hematopoietic stem cells to differentiate into macrophages or other related cell types. Eukaryotic cells also produce M-CSF to combat intercellular viral infection. It an experimentally described colony-stimulating factor. M-CSF binds to the colony stimulating factor 1 receptor. It may also be involved in placental development.

The drug to regulate the lymphatic system may inhibit colony stimulating factor 1 receptor (CSFR1). The drug to regulate the lymphatic system may antagonize CSFR1. Also known as macrophage colony-stimulating factor receptor (M-CSFR), and CD115 (Cluster of Differentiation 115), this target is a cell-surface protein encoded, in humans, by the CSF1R gene (known also as c-FMS). It is a receptor for a cytokine called colony stimulating factor 1.

The drug to regulate the lymphatic system may inhibit Chemokine (C-C motif) ligand 21 (CCL21). The drug to regulate the lymphatic system may antagonize CCL21. CCL21 is a small cytokine belonging to the CC chemokine family. This chemokine is also known as 6Ckine (because it has six conserved cysteine residues instead of the four cysteines typical to chemokines), exodus-2, and secondary lymphoid-tissue chemokine (SLC). The gene for CCL21 is on human chromosome 9. CCL21 elicits its effects by binding to a cell surface chemokine receptor known as CCR7.

The drug to regulate the lymphatic system may inhibit a regulator of lymphatic endothelial cell metabolism. The drug to regulate the lymphatic system may antagonizes a regulator of lymphatic endothelial cell metabolism. The drug to regulate the lymphatic system may inhibit an enzyme involved in lymphatic endothelial cell fatty acid oxidation. The drug to regulate the lymphatic system may antagonize an enzyme involved in lymphatic endothelial cell fatty acid oxidation. Non-limiting examples of drugs that inhibit or antagonize fatty acid oxidation include a 3-KAT inhibitor, such as trimetazidine and ranolazine; a CPT1 inhibitor, such as etomoxir, perhexiline, and oxfenicine; and a mitochondrial thiolase inhibitor, such as 4-bromocrotonic acid.

For example, the regulator of lymphatic endothelial cell metabolism may be a member of carnitine palmitoyltransferase I (CPT1) enzyme family. Also known as carnitine acyltransferase I, CPTI, CAT1, CoA:carnitine acyl transferase (CCAT), or palmitoylCoA transferase I, this target is a mitochondrial enzyme responsible for the formation of acyl carnitines by catalyzing the transfer of the acyl group of a long-chain fatty acyl-CoA from coenzyme A to 1-carnitine. The product is often palmitoylcarnitine, but other fatty acids may be substrates. Isoforms of CPT1 include CPT1A, CPT1B, and CPT1C. CPT1 is associated with the outer mitochondrial membrane. This enzyme can be inhibited by malonyl CoA, the first committed intermediate produced during fatty acid synthesis. Its role in fatty acid metabolism makes CPT1 important in many metabolic disorders such as diabetes. Since its crystal structure is not known, its exact mechanism of action remains to be determined.

The drug to regulate the lymphatic system may inhibit regulator of Prospero homeobox protein 1 (PROX1). The drug to regulate the lymphatic system may antagonize regulator of PROX1. PROX1 is a protein that in humans is encoded by the PROX1 gene. PROX1 is produced primarily in the dentate gyrus in the mouse, and in the dentate gyrus and white matter in humans.

A combination of drugs may regulate the lymphatic system. The drug to regulate the lymphatic system may comprise a VEGFR-2 inhibitor and a VEGFR-3 inhibitor.

A member of the vascular endothelial growth factor (VEGF) family, VEGF-C, has been shown as a growth factor for lymphatic vessels. VEGF-C is a ligand for the receptor tyrosine kinase VEGFR-3, which is expressed on lymphatic endothelial cells. VEGF-C also binds to and activates VEGFR-2, which is expressed by lymphatic and by blood endothelium and is also used by VEGF-A, a major angiogenesis factor. In tumors, VEGFR-3 is expressed by lymphatic endothelial cells and by the subset of blood vessels, but not by tumor cells. The important role of VEGF-C and VEGFR-3 signaling in developmental and postnatal lymphangiogenesis has been documented. Several studies have also shown that VEGF-C/VEGFR-3 signaling aids the spread of metastases from the primary tumor into the lymph nodes.

Several studies have also shown that an increase in lymph node metastases in mice bearing VEGF-C-expressing primary tumors correlates to an increase in distant metastases. VEGF-C increased tumor lymphangiogenesis and cancer spread to the lymph nodes, which was associated with increased metastatic burden in the lung in experimental models of breast cancer, prostate cancer and melanoma. Conversely, studies in mouse models of breast cancer, prostate cancer, and melanoma have shown that blocking VEGF-C/VEGFR-3 inhibits tumor lymphangiogenesis and prevents lymph node metastasis in the presence of a primary tumor, and so reduces the risk of distant metastasis. Based on these findings, VEGF-C/VEGFR-3-mediated lymphangiogenesis would not be considered a target for cancer treatment after the removal of the primary tumor.

Non-limiting examples of useful VEGFR-3 antagonists include, antagonist antibodies and fragments thereof, soluble polypeptides that inhibit the activity of VEGFR-3 or VEGFR-2 (e.g., an extracellular domain of a VEGFR-3 or VEGFR-2 protein or a derivative thereof), small molecule inhibitors (e.g., small molecule inhibitors of kinases and/or signaling pathways relevant for VEGFR-3 and/or VEGFR-2 signal transduction), and inhibitors of VEGFR-3 and/or VEGFR-2 expression (e.g., siRNAs, shRNAs, antisense oligonucleotides, ribozymes, etc.). The VEGFR-3 antagonist may be an anti-VEGFR-3 antibody or an antigen-binding part thereof. Such VEGFR-3 antagonists may be the monoclonal antibodies mR4-31C1, or VGX-100, or IMC-3C5, OPT-302 or molecules or compounds with similar or derivatives structures or small molecules with the same, similar or derivative structures as SAR-131675.

The VEGFR-2 antagonist may be an anti-VEGFR-2 antibody or an antigen-binding portion thereof. In one specific embodiment, such VEGFR-2 antagonist is the monoclonal antibody DC101. Such anti-VEGFR-2 antibody or the anti-VEGFR-3 antibody may can bind an extracellular domain of VEGFR-2 or VEGFR-3, respectively, and can block the interaction of VEGF-C, VEGF-D and/or VEGF-A with VEGFR-2 or VEGFR-3. In one embodiment, the antibody is capable of biding to its target (i.e., VEGFR-2 or VEGFR-3) with an affinity of at least about $1\times10^{-6}$M, of at least about $1\times10^{-7}$ M, of at least about $1\times10^{-8}$M, or of at least about $1\times10^{-9}$ M.

The anti-VEGFR-2 antibody or the anti-VEGFR-3 antibody may be, e.g., a chimeric antibody, a primatized antibody, a humanized antibody, or an antigen-binding portion thereof. Humanized antibodies may include one or more CDR from the monoclonal antibody DC101 or one or more CDR from the monoclonal antibody mR4-31C1.

The antigen-binding part of the antibody can be, e.g., an F(ab') 2, a Fab, an Fv, an scr'v, or a single domain antibody.

The VEGFR-2 antagonist or the VEGFR-3 antagonist may be a soluble polypeptide antagonist. Such soluble polypeptide antagonist comprises an extracellular domain of a VEGFR-2 protein or an extra cellular domain of a VEGFR-3 protein or an amino acid sequence that is at least 90%, at least 95%, at least 97%, or at least 99% identical to the extracellular domain of a VEGFR-2 protein or a VEGFR-3 protein. Optionally, one or more soluble peptide antagonist can further comprise a post-translational modification. Non-limiting examples of such post-translational modifications include, e.g., acetylation, carboxylation, glycosylation, phosphorylation, lipidation, acylation, addition of a non-amino acid element (such as, e.g., polyethylene glycol, a lipid, a poly- or mono-saccharide, or a phosphate), and addition of a fusion domain (such as, e.g., polyhistidine, Glu-Glu, glutathione S transferase (GST), thioredoxin, protein A, protein G, an immunoglobulin heavy chain constant region (Fc), a maltose binding protein (MBP), green fluorescent protein (GFP), or an epitope tag). Fusion domains can further comprise a protease cleavage site (such as, e.g., FactorXa or Thrombin).

The pattern of metastatic spread to the lungs seen with VEGF-C expressing cells in a MDA-MB-435/VEGF-C mouse model for breast cancer closely resembles Lymphangitic Carcinomatosis aggressive metastatic phenotype in human cancer patients. As described in greater detail below, tumors that do not express VEGF-C do not show any evidence of lymphatic involvement in the lungs, while VEGF-C helps lung lymphangiogenesis, tumor cell entry into the lung lymphatics and growth within, creating a niche for tumor expansion within the lung as well as a route for dissemination to the thoracic lymph nodes. Thus, VEGF-C expression by tumor cells drastically changes the pattern of metastatic disease and aids disease progression.

The VEGF-C/VEGFR-3 pathway and the lymphatic vessels are targets for treating established metastatic disease with cancer immune modulating therapies which can include, but are not limited to, immune checkpoint inhibitors and in the setting of a dysregulated lymphatic system, or tumor associated lymphatic invasion, lymphangitic carcinomatosis, or impaired antigen presentation, immune cell activation or priming alone or due to an impaired or dysregulated, dysfunctional or perturbed lymphatic system.

Systemic treatment with VEGFR-3 antagonistic antibodies (mR4-31C1, ImClone Systems, a subsidiary of Eli Lilly and Company, Indianapolis, Ind.) suppressed tumor lymphangiogenesis and inhibited lymph node metastasis of MDA-MB-435 cells expressing high levels of VEGF-C (MDA/VEGF-C). Furthermore, a combination therapy with a modulator of lymphatic biology, including but not limited to anti-VEGFR-3 antibodies with a cancer immune modulating therapy including, but not limited to an immune checkpoint inhibitor, is more potent in decreasing metastases than treatment with either antibody or therapy alone. The effects of a combination treatment were studied in an intervention regimen, in which the treatment began when tumors and metastases were established, four weeks after the orthotopic tumor cell inoculation into the mammary fat pads. Joint treatment with the antagonistic antibodies to VEGFR-2 and VEGFR-3 also significantly decreased lung metastases.

To understand the mechanism by which combined treatment inhibits metastasis, its effects on the primary tumor were investigated. Joint treatment did not result in greater inhibition of primary tumor growth than treatment with the anti-VEGFR-2 antibody alone. (Blocking VEGFR-3 had no effect on primary tumor growth.) Analysis of tumor vasculature showed that double-treatment was also not more potent in inhibiting tumor lymphangiogenesis or angiogenesis, as compared to single antibody treatments. These data demonstrated that the effects of combined treatment on metastases cannot be explained by changes of the tumor vasculature or growth of the primary tumor.

Events downstream from the primary tumor, i.e. in the lymph nodes, may be important for the observed inhibition of metastases with the joint treatment. The pattern of lymphatic and blood vasculature in tumor draining lymph nodes of control and treated mice was examined by immunofluorescent staining using LYVE-1 and CD34 antibodies, respectively. The results showed that MDA-MB-435/VEGF-C tumors induced prominent lymphangiogenesis in tumor draining axillary lymph nodes. LYVE-1 lymphatic vessels were restricted to medullary zone and subcapsular sinuses, while no LYVE-1 structures were seen in the lymph node cortex. Tumor draining lymph nodes increased in size when compared to control lymph nodes of normal mice.

Blocking VEGFR-3 reduced the lymphatic vessel area and lymph node size in the tumor-draining lymph nodes to a moderate extent. Blocking VEGFR-2 showed moderate inhibition of lymphangiogenesis and a more prominent inhibition of lymph node size. Joint blocking of VEGFR-3 and VEGFR-2 drastically inhibited lymph node lymphangiogenesis and dramatically reduced lymph node size.

Taken together, analysis of tumor draining lymph nodes revealed that joint blocking of VEGFR-3 and VEGFR-2 was most effective in inhibiting lymph node lymphangiogenesis and lymph node size, as compared to single antibody treatments. These data showed the importance of concurrent VEGFR-2 and VEGFR-3 signaling for lymph node lymphangiogenesis and strongly indicated an important role of lymph node lymphangiogenesis for both lymph node and distant metastases.

The effects of antagonistic antibodies to VEGFR-2 and VEGFR-3 on tumor-induced lymph node angiogenesis were examined. Comparison of the CD34+ vessel pattern in normal and tumor draining lymph nodes showed an increase in the density of blood microvasculature within the lymph node cortex, while the density of blood microvasculature was not altered. Tumors induced angiogenesis in tumor draining lymph nodes by 80%. Interestingly, the increase in total number of blood vessels was directly correlated to the increase of lymph node size associated with the tumor, showing that the blood vessel density per lymph node area stayed unchanged.

Blocking VEGFR-3 alone did reduce the lymph node blood vessel density. Blocking VEGFR-2 drastically reduced blood vessel density (50%). Joint blocking of VEGFR-2 and VEGFR-3 reduced blood vessel numbers slightly more (64%). Thus, the combination treatment, with antagonistic antibodies to both VEGFR-2 and VEGFR-3 is most effective for the inhibition of lymph node lymphangiogenesis and lymph node size.

VEGF-C expression by tumor cells potently increased metastatic burden in the lungs. To further understand the mechanism by which VEGF-C and its receptors aid formation of distant metastases, the phenotype of lung metastases formed by MDA-MB-435 and MDA-MB-435/VEGF-C cells was examined. These cells were injected orthotopically into the second mammary fat pads of nude mice and tumors and metastases could develop for 12 weeks. Tumor size reached an average volume of about 1 cm after the 12-week period. At the end of the experiment (12 weeks), 8 out of 8 mice (100%) bearing MDA-MB-435 cells or MDA-MB-435/VEGF-C cells had a positive signal in the lungs.

Histopathological analysis of metastases revealed a distinct pattern of pulmonary metastases by tumor cells expressing high levels of VEGF-C. MDA MB-435/VEGF-C cells showed a unique distribution in the lung as compared to the non-VEGF-C expressing cells. Metastases from MDA-MB-435/VEGF-C cells presented as large lesions associated with the bronchi and large pulmonary vessels. In contrast, metastases of MDA-MB-435 control cells presented as small pulmonary nodules that localized in the lung parenchyma and were not associated with the bronchi. Smooth muscle 0-actin staining of the large pulmonary vessels and airways further showed that metastases from MDA-MB-435 cells had no affiliation with the large pulmonary vasculature and were often distant from large vessels, while VEGF-C overexpressing lesions were often seen in intravascular emboli, localizing in pulmonary arteries. These results show that increased VEGF-C production by metastatic cells resulted in an increase in lung metastasis and drives a phenotype in which tumor cells are often seen as endovascular nodules in the peribronchovascular region.

Lymphatic vessels in lungs infiltrated with MDA/pcDNA tumor cells were detected in their normal anatomical location, i.e. surrounding bronchi, large pulmonary vessels and in the pleura, and they were not altered in their appearance compared to normal lungs not involved with cancer. There was no lymphangiogenesis associated with MDA/pcDNA nodules, and only seldom were lymphatics seen near these nodules (number of metastatic foci with lymphatics present within 200 pum:MDA/pcDNA 6/48; 13% vs. MDA/VEGF-C 37/39; 95%). In contrast, VEGF-C-overexpressing metastatic lesions had pronounced lymphangiogenesis, and lymphatic vessels were distended throughout the lungs with MDA/VEGF-C metastases. Lymphatic vessel area associated with MDA/VEGF-C metastatic foci was on average 75-fold greater than lymphatic vessel area associated with MDA/pcDNA foci which had lymphatics in the proximity. Expansion of lymphatic network paralleled an increase in size of MDA/VEGF-C metastases.

Because most VEGF-C overexpressing metastases were found next to bronchi, the relationship between MDA/VEGF-C metastases and the deep lymphatic plexus associated with the bronchial tree was investigated. Lymphatic vessels were detected by using a combination of anti-LYVE-1, anti-podoplanin, and anti-VEGFR-3 antibodies. Strikingly, bulk of MDA/VEGF-C metastases seen in the peribronchial area was seen inside of the distended lymphatic vessels (31/55 metastatic foci showed lymphatic vessel involvement; 56%). Lymphatic vessels near pulmonary veins were also massively infiltrated with tumor cells. Furthermore, MDA/VEGF-C metastases were often detected in the pleura (MDA/VEGF-C in 5/7 mice; MDA/pcDNA in 1/6 mice), which is another area of lung tissue rich in lymphatics. In sharp contrast, MDA/pcDNA metastases were rarely seen intravascular or even near the lymphatic vasculature. These data show that VEGF-C aid intralymphatic spread of metastases in the lung.

To investigate whether VEGF-C promotes secondary metastatic dissemination, within the lymphatic network in the lung, lung-draining lymph nodes were analyzed for metastases. At necropsy, mediastinal and hilar lymph nodes from mice bearing VEGF-C overexpressing and control MDA-MB-435 tumors were evaluated using stereomicroscopy to detect the GFP fluorescence. The incidence of lymph nodes positive for metastases from VEGF-C overexpressing tumor bearing mice was significantly higher (13/20, 65%) than in mice bearing control tumors (3/20, 15%). To confirm the presence of tumor cells and to analyze the specific area of the metastases within the mediastinal or hilar lymph nodes, the histopathology of lymph nodes from mice bearing the VEGF-C over-expressing tumors was studied. Using podoplanin as a lymphatic vessel marker, metastases were seen in the subcapsular sinus region. These data showed that VEGF-C promotes lymphatic spread of metastases within the lung, promoting secondary tumor spread to the thoracic lymph nodes.

The finding that VEGF-C induces aggressive lymphangitic carcinomatosis phenotype in a mouse breast cancer model suggested that VEGF-C and its receptor VEGFR-3 and/or VEGFR-2 could be targets for treating this disease. Because in most cancer patients with cancer primary tumor is removed (unless it is unresectable), an experiment was designed in which VEGFR-3 signaling was inhibited with antagonistic antibodies after the removal of the primary tumor. VEGF-C overexpressing MDA-MB-435 cells were orthotopically injected into the second mammary fat pad of nu/nu mice and tumor and lung metastases could develop for 8 weeks. The extent of metastases was monitored and quantified by in vivo bioluminescent imaging. At the 8th week, the primary tumor was surgically removed and function-blocking antibodies to VEGFR-3 (mP4-31C1, ImClone Systems) were administered at 800 pg/mouse every second day and metastases were analyzed after six weeks of treatment.

A stark contrast between the metastatic patterns between the control and the mP4-31C1 treated groups was seen, as assessed by histopathological analysis of lung sections. Control samples (MDA/VEGF-C cells) showed many intravascular metastases seen in the pulmonary arteries associated with the bronchial tree, and in the lymphatic vessels of the peribronchovascular region, around the pulmonary veins, and in the pleura. Conversely, in lung sections from the mice treated with anti-VEGFR-3 antibodies, metastases were seen primarily in the lung parenchyma and capillaries of the lungs, and were less often associated with lymphatics, pulmonary arteries, or the bronchial tree. Metastases associated with the airways were not found in the lymphatic vessels or in the pulmonary arteries, and there was no lymphangiogenesis. Typical phenotype of VEGF-C expressing metastases grow in the lymphatic vessels and present as pulmonary artery tumoremboli. Collectively, these data showed that VEGF-C/VEGFR-3 signaling has a significant role in driving breast adenocarcinoma metastases towards the clinical manifestation of lymphangitic carcinomatosis and that inhibition of VEGFR-3 can reverse this aggressive phenotype.

C. Immune modulating therapy

The immune modulating therapy may be selected from the group consisting of an antagonist for immune checkpoint inhibition, an agonist for immune co-stimulation signal, a stimulatory factor affecting immune cell priming and activation, a chemotactic agent, cytokine-related immune modulator, chemotherapeutic immune stimulation, radiotherapeutic immune stimulation, a vaccine, activation of an adaptive immune response, and activation of an innate immune response. Immune modulating therapy that work independent of immune cell priming and antigen presentation include adoptive cell transfer and immune cell modification strategies, such as chimeric antigen receptor T cell (CAR-T) therapy. Here, immune cells are changed (1) intrinsically (in vivo modification which would include vaccination-based approaches and the like), (2) extrinsically via adoptive cell therapies or immune cell modification strategies, such as via CAR-T therapy, immune cell grafting, immune cell transplantation, or stem cell transplantation, and related strategies, and any combination of intrinsic or extrinsic modification.

The immune modulating therapy may be an antagonist for immune checkpoint inhibition. The immune modulating therapy may be an agonist for immune co-stimulation signal. The immune modulating therapy may be a stimulatory factor affecting immune cell priming and activation. The immune modulating therapy may be a chemotactic agent. The immune modulating therapy may be cytokine-related immune modulator. The immune modulating therapy may be chemotherapeutic immune stimulation. The immune modulating therapy may be radiotherapeutic immune stimulation. The immune modulating therapy may be a vaccine. The immune modulating therapy may be activation of an adaptive immune response. The immune modulating therapy may be activation of an innate immune response.

The immune modulating therapy may be an antagonist for immune checkpoint inhibition having a target selected from the group consisting of PD-1, PD-L1, CTLA-4, LAG3, TIM-2, CD47, KIR, TIM3, and CD30.

The target may be programmed cell death protein 1(PD-1), also known as and CD279 (cluster of differentiation 279).

PD-1 is a cell surface receptor that downregulates the immune system and promote self-tolerance by suppressing T cell inflammatory activity. PD-1 is an immune checkpoint and guards against autoimmunity through a dual mechanism of promoting apoptosis (programmed cell death) in antigen specific T-cells in lymph nodes while simultaneously reducing apoptosis in regulatory T cells (anti-inflammatory, suppressive T cells). PD-1 inhibits the immune system. This prevents autoimmune diseases, but it can also prevent the immune system from killing cancer cells. Drugs that block PD-1, the PD-1 inhibitors, activate the immune system to attack tumors PD-1 is a cell surface receptor that belongs to the immunoglobulin superfamily and is expressed on T cells and pro-B cells. PD-1 binds two ligands, PD-L1 and PD-L2.

The target may be programmed death-ligand 1 (PD-L1). Also known as cluster of differentiation 274 (CD274) or B7 homolog 1 (B7-H1), PD-L1 is a protein that in humans is encoded by the CD274 gene. Programmed death-ligand 1 (PD-L1) is a 40 kDa type 1 transmembrane protein may suppress the immune system during pregnancy, tissue allografts, autoimmune disease, and hepatitis. Normally, the immune system reacts to foreign antigens associated with exogenous or endogenous danger signals, which trigger a proliferation of antigen-specific CD8+ T cells and/or CD4+ helper cells. The binding of PD-L1 to PD-1 or B7.1 transmits an inhibitory signal that reduces the proliferation of these T cells and can also induce apoptosis, which is further mediated by a lower regulation of the gene Bcl-2.

The target may be cytotoxic T-lymphocyte-associated protein 4 (CTLA-4), also known as CD152 (cluster of differentiation 152). CTLA-4 is a protein receptor that, functioning as an immune checkpoint, downregulates immune responses. CTLA4 is constitutively expressed in regulatory T cells but only upregulated in conventional T cells after activation.

The target may be lymphocyte-activation gene 3 (LAG-3), a protein which in humans is encoded by the LAG3 gene. LAG3 is also designated CD223 (cluster of differentiation 223). LAG3 is a cell surface molecule with diverse biologic effects on T cell function. It is an immune checkpoint receptor.

The target may be T cell immunoglobulin and mucin domain family 2 (TIM-2) for family 3 (TIM3).

The target may be Cluster of Differentiation 47 (CD47), also known as integrin associated protein (TAP). CD47 is a transmembrane protein that in humans is encoded by the CD47 gene. CD47 belongs to the immunoglobulin superfamily and partners with membrane integrins and binds the ligands thrombospondin-1 (TSP-1) and signal-regulatory protein alpha (SIRPα). This is because the protein IAP produced by CD-47 acts as a don't eat me signal to the immune system and drives organ fibrosis. CD47 is involved in many cellular processes, including apoptosis, proliferation, adhesion, and migration. Furthermore, it plays a key role in immune and angiogenic responses. CD47 is ubiquitously expressed in human cells and has been found to be overexpressed in many different tumor cells. Expression in equine cutaneous tumors has been reported as well.

The target may be killer-cell immunoglobulin-like receptors (KIR), a family of type I transmembrane glycoproteins expressed on the plasma membrane of natural killer (NK) cells and a minority of T cells.

The target may be CD30. CD30, also known as TNFRSF8, is a cell membrane protein of the tumor necrosis factor receptor family and tumor marker. This receptor is expressed by activated, but not by resting, T and B cells. TRAF2 and TRAF5 can interact with this receptor, and mediate the signal transduction that leads to the activation of NF-kappaB. It is a positive regulator of apoptosis, limits the proliferative potential of autoreactive CD8 effector T cells, and protect the body against autoimmunity. Two alternatively spliced transcript variants of this gene encoding distinct isoforms have been reported.

The immune modulating therapy may be an agonist for immune co-stimulation signal having a target selected from the group consisting of CD137/41BB, 41BBL, OX40, CD27, CD40/CD40L/cd40/CEA-CD3CD, and STING.

The target may be CD137/41BB. CD137 is a member of the tumor necrosis factor (TNF) receptor family. Its alternative names are tumor necrosis factor receptor superfamily member 9 (TNFRSF9), 4-1BB and induced by lymphocyte activation (ILA). CD137 can be expressed by activated T cells, but on CD8 than on CD4 T cells. In addition, CD137 expression is found on dendritic cells, B cells, follicular dendritic cells, natural killer cells, granulocytes and cells of blood vessel walls at sites of inflammation.

The target may be 4-1BB, a type 2 transmembrane glycoprotein belonging to the TNF superfamily, expressed on activated T lymphocytes. 41BBL is the ligand for 4-1BB.

The target may be OX40. Tumor necrosis factor receptor superfamily, member 4 (TNFRSF4), also known as CD134 and OX40 receptor, is a member of the TNFR-superfamily of receptors which is not constitutively expressed on resting naïve T cells, unlike CD28. OX40 is a secondary co-stimulatory immune checkpoint molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels.

The target may be cluster of differentiation 27 (CD27), a member of the tumor necrosis factor receptor superfamily and a co-stimulatory immune checkpoint molecule. The protein encoded by this gene is a member of the TNF-receptor superfamily. This receptor is needed for generation and long-term maintenance of T cell immunity. It binds to ligand CD70, and regulate B-cell activation and immunoglobulin synthesis. This receptor transduces signals that lead to the activation of NF-κB and MAPK8/JNK. Adaptor proteins TRAF2 and TRAF5 have been shown to mediate the signaling process of this receptor. CD27-binding protein (SIVA), a proapoptotic protein, can bind to this receptor and induces apoptosis by this receptor.

The target may be cluster of differentiation 40 or its ligand CD40/CD40L/cd40/CEA-CD3CD. CD40 is a costimulatory protein found on antigen presenting cells and is needed for their activation. Binding CD154 (CD40L) on TH cells to CD40 activates antigen presenting cells and induces a variety of downstream effects. Deficiency can cause Hyper-IgM syndrome type 3.

The target may be stimulator of interferon genes (STING), also known as transmembrane protein 173 (TMEM173) and MPYS/MITA/ERIS. STING is a protein that in humans is encoded by the TMEM173 gene.

The immune modulating therapy may be a stimulatory factor affecting immune cell priming and activation selected from the group consisting of CD28/B7.1, CD137/CD137L, OX40/OX40L, CD27/CD70, HVEM, GITR, CDN, ATB, HMGB1, TLR4, LR7, TLR 8, TLR9, MICA/MICB, B7-H2, B7-H3, B7-H4, and B7-1/2.

The stimulatory factor may be Cluster of Differentiation 28(CD28/B7.1), one of the proteins expressed on T cells that provide co-stimulatory signals for T cell activation and survival. T cell stimulation through CD28 in addition to the T-cell receptor (TCR) can provide a potent signal for producing various interleukins (IL-6 in particular). CD28 is the receptor for CD80 (B7.1) and CD86 (B7.2) proteins. When activated by Toll-like receptor (TLR) ligands, the CD80 expression is upregulated in antigen presenting cells (APCs). The CD86 expression on antigen presenting cells is constitutive (expression is independent of environmental factors). CD28 is the only B7 receptor constitutively expressed on naive T cells. Association of the TCR of a naive T cell with MHC:antigen complex without CD28:B7 interaction results in a T cell that is anergic.

The stimulatory factor may be CD137/CD137L. CD137 is a member of the tumor necrosis factor (TNF) receptor family. Its alternative names are tumor necrosis factor receptor superfamily member 9 (TNFRSF9), 4-1BB and induced by lymphocyte activation (ILA). CD137 is a co-stimulatory immune checkpoint molecule.

The stimulatory factor may be OX40/OX40L. The stimulatory factor may be CD27/CD70.

The stimulatory factor may be herpesvirus entry mediator (HVEM), also known as tumor necrosis factor receptor superfamily member 14 (TNFRSF14), is a human cell surface receptor of the TNF-receptor superfamily.

The stimulatory factor may be GITR. Tumor necrosis factor receptor superfamily member 18 (TNFRSF18) also known as activation-inducible TNFR family receptor (AITR) or glucocorticoid-induced TNFR-related protein (GITR) is a protein that in humans is encoded by the TNFRSF18 gene. GITR is a co-stimulatory immune checkpoint molecule.

The stimulatory factor may be CDN. The stimulatory factor may be ATB.

The stimulatory factor may be high mobility group box 1 protein, also known as high-mobility group protein 1 (HMG-1) and amphoterin, a protein that in humans is encoded by the HMGB1 gene. In the nucleus HMGB1 interacts with nucleosomes, transcription factors, and histones. This nuclear protein organizes the DNA and regulates transcription. After binding, HMGB1 bends DNA, which aids binding of other proteins. HMGB1 supports transcription of many genes in interactions with many transcription factors. It also interacts with nucleosomes to loosen packed DNA and remodel the chromatin. Contact with core histones changes the structure of nucleosomes. HMGB1 in the nucleus depends on posttranslational modifications. When the protein is not acetylated, it stays in the nucleus, but hyperacetylation on lysine residues causes it to translocate into the cytosol. HMGB1 has been shown to play an important role in helping the RAG endonuclease form a paired complex during V(D)J recombination. HMG-1 belongs to high mobility group and contains HMG-box domain.

The stimulatory factor may be toll-like receptor 4 (TLR4). a transmembrane member of the toll-like receptor family, which belongs to the pattern recognition receptor (PRR) family. Its activation leads to an intracellular signaling pathway NF-κB and inflammatory cytokine production responsible for activating the innate immune system. TLR4 is most well-known for recognizing lipopolysaccharide (LPS), a component present in many Gram-negative bacteria (e.g. *Neisseria* spp.) and select Gram-positive bacteria. Its ligands also include several viral proteins, polysaccharide, and a variety of endogenous proteins such as low-density lipoprotein, beta-defensins, and heat shock protein. TLR4 has also been designated as CD284 (cluster of differentiation 284).

The stimulatory factor may be toll-like receptor 7 (TLR7), a protein that in humans is encoded by the TLR7 gene. TLR7 recognizes single-stranded RNA in endosomes, a common feature of viral genomes which are internalized by macrophages and dendritic cells. TLR7 recognizes single-stranded RNA of viruses such as HIV and HCV. TLR7 can recognize GU-rich single-stranded RNA. However, the presence of GU-rich sequences in the single-stranded RNA is not enough to stimulate TLR7.

The stimulatory factor may be toll-like receptor 8 (TLR8). Also known as cluster of differentiation 288 (CD288), TLR8 a protein that in humans is encoded by the TLR8 gene. TLR8 can recognize GU-rich single-stranded RNA. However, the presence of GU-rich sequences in the single-stranded RNA is not enough to stimulate TLR8. TLR8 recognizes G-rich oligonucleotides. TLR8 is an endosomal receptor that recognizes single stranded RNA (ssRNA), and can recognize ssRNA viruses such as Influenza, Sendai, and Coxsackie B viruses. TLR8 binding to the viral RNA recruits MyD88 and leads to activation of the transcription factor NF-κB and an antiviral response. TLR8 recognizes single-stranded RNA of viruses such as HIV and HCV.

The stimulatory factor may be toll-like receptor 9 (TLR9), also known as CD289 (cluster of differentiation 289). TLR9 is a member of the toll-like receptor (TLR) family. TLR9 is an important receptor expressed in immune system cells including dendritic cells, macrophages, natural killer cells, and other antigen presenting cells. TLR9 preferentially binds DNA present in bacteria and viruses, and triggers signaling cascades that lead to a pro-inflammatory cytokine response. Cancer, infection, and tissue damage can all modulate TLR9 expression and activation. TLR9 is also an important factor in autoimmune diseases, and there is active research into synthetic TLR9 agonists and antagonists that help regulate autoimmune inflammation.

The stimulatory factor may be major histocompatibility complex (MHC) class I polypeptide-related sequence A (MICA) is a cell surface glycoprotein encoded by the MICA gene within MHC locus. MICA is related to MHC class I and has similar domain structure, which is made up of external α1α2α3 domain, transmembrane segment and C-terminal cytoplasmic tail. However, MICA is not associated with β2-microglobulin nor binds peptides as conventional MHC class I molecules do. MICA works as a stress-induced ligand for NKG2D receptor. For example, the heat shock stress pathway regulates MICA expression as transcription of MICA is regulated by promoter heat shock element. MICA is broadly recognized by NK cells, γδ T cells, and CD8+αβ T cells which carry NKG2D receptor on their cell surface. Because of NKG2D-MICA engagement, effector cytolytic responses of T cells and NK cells against epithelial tumor cells expressing MICA are started.

The stimulatory factor may be major histocompatibility complex (MHC) class I polypeptide-related sequence B (MICB) is a protein that is encoded by the MICB gene within MHC locus. MICB is related to MHC class I and has similar domain structure, which is made up of external α1α2α3 domain, transmembrane segment and C-terminal cytoplasmic tail. MICB is a stress-induced ligand for NKG2D receptor. The heat shock stress pathway is involved in the regulation of MICB expression as transcription of MICB is regulated by promoter heat shock element.

The stimulatory factor may be a B7 protein. B7 is a type of peripheral membrane protein found on activated antigen presenting cells (APC) that, when paired with either a CD28 or CD152 (CTLA-4) surface protein on a T cell, can produce a costimulatory signal or a coinhibitory signal to enhance or decrease the activity of a MHC-TCR signal between the APC and the T cell, respectively. Binding the B7 of APC to CTLA-4 of T-cells causes inhibition of the activity of T-cells. There are two major types of B7 proteins: B7-1 or CD80, and B7-2 or CD86. However, it is not known if they differ significantly from each other. CD28 and CTLA-4 each interact with both B7-1 and B7-2. The stimulatory factor may be B7-H2. The stimulatory factor may be B7-H3. The stimulatory factor may be B7-H4. The stimulatory factor may be B7-1/2.

The immune modulating therapy may be a chemotactic agent selected from the group consisting of CX3CL1, CXCL9, CXCL10, CCL5, LFA1, ICAM1, selectin E, selectin P, selectin N, CXCR4, CCR2, CCL21, CCR5, CXCR1, CXCR2, CSF1R, and CCR4. The chemotactic agent may be a chemokine, a small protein that regulates cell trafficking of leukocytes. The chemokines also play fundamental roles in the development, homeostasis, and function of the immune system, and they have effects on cells of the central nervous system as well as on endothelial cells involved in angiogenesis or angiostasis.

The chemotactic agent may be CX3CL1. Fractalkine, also known as chemokine (C-X3-C motif) ligand 1, is a protein that in humans is encoded by the CX3CL1 gene. Fractalkine is a large cytokine protein of 373 amino acids, it has multiple domains and is the only known member of the CX3C chemokine family. The polypeptide structure of CX3CL1 differs from the typical structure of other chemokines.

The chemotactic agent may be chemokine (C-X-C motif) ligand 9 (CXCL9), a small cytokine belonging to the CXC chemokine family that is also known as monokine induced by gamma interferon (MIG). CXCL9 is a T-cell chemoattractant, which is induced by IFN-γ. It is closely related to two other CXC chemokines called CXCL10 and CXCL11, whose genes are near the gene for CXCL9 on human chromosome 4. CXCL9, CXCL10 and CXCL11 all elicit their chemotactic functions by interacting with the chemokine receptor CXCR3. Neutrophil collagenase/matrix metalloproteinase 8 (MMP-8) degrades CXCL9 and cleaves CXCL10 at two positions. Gelatinase B/matrix metalloproteinase 9 (MMP-9) degrades CXCL10 and cleaves CXCL9 at three different sites in its extended carboxy-terminal region.

The chemotactic agent may be C-X-C motif chemokine 10 (CXCL10), also known as interferon gamma-induced protein 10 (IP-10) or small-inducible cytokine B10. CXCL10 is an 8.7 kDa protein that in humans is encoded by the CXCL10 gene.

The chemotactic agent may be chemokine (C-C motif) ligand 5 (CCL5), a protein which in humans is encoded by the CCL5 gene. It is also known as RANTES (regulated on activation, normal T cell expressed and secreted).

The chemotactic agent may be lymphocyte function-associated antigen 1 (LFA-1), found on T-cells, B-cells, macrophages, neutrophils and NK cells. LFA1 is involved in recruitment to the site of infection. It binds to ICAM-1 on antigen-presenting cells and functions as an adhesion molecule. LFA-1 is the first to bind T-cells to antigen-presenting cells and initially binds weakly. A signal from the T-cell receptor and/or the cytokine receptor changes the conformation and prolongs the cell contact, allowing the T-cell to proliferate. LFA-1/ICAM-1 interaction leads to further T cell differentiation. LFA-1 is part of the family of leukocyte integrins recognized by their common β-chains (β2, CD18). LFA-1 also has a distinct a-chain (αL, CD11a).

The chemotactic agent may be Intercellular Adhesion Molecule 1 (ICAM-1), also known as CD54 (Cluster of Differentiation 54). ICAM-1 is a protein that in humans is encoded by the ICAM1 gene, giving a cell surface glycoprotein typically expressed on endothelial cells and cells of the immune system. It binds to integrins of type CD11a/CD18, or CD11b/CD18 and is also exploited by rhinovirus as a receptor.

The chemotactic agent may be one or more selectins. The selectins (cluster of differentiation 62 or CD62) are a family of cell adhesion molecules (or CAMs). All selectins are single-chain transmembrane glycoproteins that share similar properties to C-type lectins due to a related amino terminus and calcium-dependent binding. Selectins bind to sugar moieties and so are a type of lectin, cell adhesion proteins that bind sugar polymers. The chemotactic agent may be selectin E. The chemotactic agent may be selectin P. The chemotactic agent may be selectin N.

The chemotactic agent may be CXCR4. C-X-C chemokine receptor type 4 (CXCR-4) also known as fusin or CD184 (cluster of differentiation 184) is a protein that in humans is encoded by the CXCR4 gene.

The chemotactic agent may be C-C chemokine receptor type 2 (CCR2) also known as cluster of differentiation 192 (CD192), a protein that in humans is encoded by the CCR2 gene. CCR2 is a chemokine receptor. This gene encodes two isoforms of a receptor for monocyte chemoattractant protein-1 (CCL2), a chemokine which specifically mediates monocyte chemotaxis. Monocyte chemoattractant protein-1 is involved in monocyte infiltration in inflammatory diseases, such as rheumatoid arthritis, and in the inflammatory response against tumors. The receptors encoded by this gene mediate agonist-dependent calcium mobilization and inhibition of adenylyl cyclase.

The chemotactic agent may be chemokine (C-C motif) ligand 21 (CCL21), a small cytokine belonging to the CC chemokine family. This chemokine is also known as 6Ckine (because it has six conserved cysteine residues instead of the four cysteines typical to chemokines), exodus-2, and secondary lymphoid-tissue chemokine (SLC). The gene for CCL21 is on human chromosome 9. CCL21 elicits its effects by binding to a cell surface chemokine receptor known as CCR7.

The chemotactic agent may be C-C chemokine receptor type 5 (CCR5), also known as cluster of differentiation 195 (CD195), a protein on the surface of white blood cells involved in the immune system, as it acts as a receptor for chemokines. This is the process by which T cells are attracted to specific tissue and organ targets. Many forms of HIV, the virus that causes AIDS, initially use CCR5 to enter and infect host cells. Certain individuals carry a CCR5-432 mutation in the CCR5 gene, protecting them against these strains of HIV.

The chemotactic agent may be C-X-C motif chemokine receptor 1 (CXCR1), also known as interleukin 8 receptor, alpha (IL8RA) and cluster of differentiation 181 (CD181). The protein encoded by this gene is a member of the G-protein-coupled receptor family. This protein is a receptor for interleukin 8 (IL8). It binds to IL8 with high affinity, and transduces the signal through a G-protein-activated second messenger system. Knockout studies in mice suggested that this protein inhibits embryonic oligodendrocyte precursor migration in developing spinal cord. This gene, IL8RB, a gene encoding another high affinity IL8 receptor, and IL8RBP, a pseudogene of IL8RB, form a gene cluster in a region mapped to chromosome 2q33-q36. Stimulation of CXCR1 in neutrophils by its primary ligand, Interleukin 8, leads to neutrophil chemotaxis and activation.

The chemotactic agent may be CXCR2, also known as interleukin 8 receptor, beta (IL8RB). The protein encoded by this gene is a member of the G-protein-coupled receptor family. This protein is a receptor for interleukin 8 (IL8). It binds to IL8 with high affinity, and transduces the signal through a G-protein-activated second messenger system (Gi/o-coupled). This receptor also binds to chemokine (C-X-C motif) ligand 1 (CXCL1/MGSA), a protein with melanoma growth stimulating activity, and is a major component for serum-dependent melanoma cell growth. In addition, it binds ligands CXCL2, CXCL3, and CXCL5. The angiogenic effects of IL8 in intestinal microvascular endothelial cells are found to be mediated by this receptor. Knockout studies in mice suggested that this receptor controls the positioning of oligodendrocyte precursors in developing spinal cord by arresting their migration. This gene, IL8RA, a gene encoding another high affinity IL8 receptor, and IL8RBP, a pseudogene of IL8RB, form a gene cluster in a region mapped to chromosome 2q33-q36. Mutations in CXCR2 cause hematological traits.

The chemotactic agent may be colony stimulating factor 1 receptor (CSF1R), also known as macrophage colony-stimulating factor receptor (M-CSFR), and CD115 (Cluster of Differentiation 115), a cell-surface protein encoded, in humans, by the CSF1R gene (known also as c-FMS). It is a receptor for a cytokine called colony stimulating factor 1. The encoded protein is a single pass type I membrane protein and acts as the receptor for colony stimulating factor 1, a cytokine which controls the production, differentiation, and function of macrophages. This receptor mediates most, if not all, of the biological effects of this cytokine. Ligand binding activates CSF1R through a process of oligomerization and trans-phosphorylation. The encoded protein is a tyrosine kinase transmembrane receptor and member of the CSF1/PDGF receptor family of tyrosine-protein kinases.

The chemotactic agent may be CCR4. C-C chemokine receptor type 4 is a protein that in humans is encoded by the CCR4 gene. CCR4 has also recently been designated CD194 (cluster of differentiation 194). The protein encoded by this gene belongs to the G protein-coupled receptor family. It is a receptor for the CC chemokines CCL2 (MCP-1), CCL4 (MIP-1), CCL5 (RANTES), CCL17 (TARC), and CCL22 (Macrophage-derived chemokine).

The immune modulating therapy may be a chemotactic agent comprising a cytokine selected from the group consisting of IL-1, IL-2, IL-4, IL-6, IL-7, IL-8, IL-13, IL-12, interferon gamma, IFNa, TNFa, CSF1, CSF1R, and GM-CSF.

The chemotactic agent may be the interleukin-1 family (IL-1 family), a group of 11 cytokines, which regulate immune and inflammatory responses to infections or sterile insults.

The chemotactic agent may be interleukin 2 (IL-2), a cytokine glycoprotein that stimulates the growth of T cell lymphocytes and provides other biochemical signaling to the immune system.

The chemotactic agent may be interleukin 4 (IL4, IL-4), a cytokine that induces differentiation of naive helper T cells (Th0 cells) to Th2 cells. Upon activation by IL-4, Th2 cells then produce more IL-4 in a positive feedback loop. Basophils may initially produce IL-4, thus inducing Th0 differentiation. IL-2 is closely related and has functions like interleukin 13.

The chemotactic agent may be interleukin 6 (IL-6), a pro-inflammatory cytokine.

The chemotactic agent may be interleukin 7 (IL-7), a protein that in humans is encoded by the IL7 gene. IL-7 is a hematopoietic growth factor secreted by stromal cells in the bone marrow and thymus. IL-7 is also produced by keratinocytes, dendritic cells, hepatocytes, neurons, and epithelial cells, but not by normal lymphocytes.

The chemotactic agent may be interleukin 8 (IL-8), a chemokine of the immune system The chemotactic agent may be interleukin 13 (IL-13), a protein that in humans is encoded by the IL13 gene. IL-13 is on chromosome 5q31 with a length of 1.4 kb. IL-13 and IL-4 show a 30% of sequence similarity and have a similar structure. IL-13 is cytokine secreted by many cell types, but especially T helper type 2 (Th2) cells; that is, a mediator of allergic inflammation and disease.

The chemotactic agent may be interleukin 12 (IL-12), an interleukin naturally produced by dendritic cells, macrophages, neutrophils, and human B-lymphoblastoid cells (NC-37) in response to antigenic stimulation. IL-12 is involved in the differentiation of naive T cells into Th1 cells. IL-12 is known as a T cell-stimulating factor, which can stimulate the growth and function of T cells. It stimulates the production of interferon-gamma (IFN-γ) and tumor necrosis factor-alpha (TNF-α) from T cells and natural killer (NK) cells, and reduces IL-4 mediated suppression of IFN-γ. T cells that produce IL-12 have a coreceptor, CD30, which is associated with IL-12 activity.

The chemotactic agent may be interferon gamma (IFNγ), a dimerized soluble cytokine and is the only member of the type II class of interferons.

The chemotactic agent may be IFN-α, which are proteins are produced by leukocytes. They are involved in innate immune response against viral infection. The genes responsible for their synthesis come in 13 subtypes that are called IFNA1, IFNA2, IFNA4, IFNA5, IFNA6, IFNA7, IFNA8, IFNA10, IFNA13, IFNA14, IFNA16, IFNA17, IFNA21. These genes are found together in a cluster on chromosome 9. The recombinant type is interferon alfacon-1. The pegylated types are pegylated interferon alfa-2a and pegylated interferon alfa-2b.

The chemotactic agent may be tumor necrosis factor (TNF, tumor necrosis factor alpha, TNFα, cachexin, or cachectin), a cell signaling protein (cytokine) involved in systemic inflammation. TNFα is one of the cytokines that makes up the acute phase reaction. TNFα is produced chiefly by activated macrophages, although it can be produced by many other cell types such as CD4+ lymphocytes, NK cells, neutrophils, mast cells, eosinophils, and neurons. TNF primarily regulates immune cells. TNF, being an endogenous pyrogen, can induce fever, apoptotic cell death, cachexia, inflammation and to inhibit tumorigenesis and viral replication and respond to sepsis via IL1 and IL6 producing cells. Dysregulation of TNF production has been implicated in a variety of human diseases including Alzheimer's disease, cancer, major depression, psoriasis and inflammatory bowel disease (IBD). Though controversial, studies of depression and IBD are linked to TNF levels. Recombinant TNF is used as an immunostimulant under the INN tasonermin. TNF can be produced ectopically in the setting of malignancy and parallels parathyroid hormone both in causing secondary hypercalcemia and in the cancers with which excessive production is associated.

The chemotactic agent may be CSF1. The chemotactic agent may be CSF1R.

The chemotactic agent may be granulocyte-macrophage colony-stimulating factor (GM-CSF), also known as colony stimulating factor 2 (CSF2), a monomeric glycoprotein secreted by macrophages, T cells, mast cells, natural killer cells, endothelial cells and fibroblasts that functions as a cytokine. The pharmaceutical analogs of naturally occurring GM-CSF are called sargramostim and molgramostim. Unlike granulocyte colony-stimulating factor, which specifically promotes neutrophil proliferation and maturation, GM-CSF affects more cell types, especially macrophages and eosinophils.

The immune modulating therapy may be chemotherapeutic immune stimulation selected from the group consisting of cyclophosphamide, paclitaxel, doxorubicin, TDO2, ARG1, ARG2, PDE5, P2X7 inhibitor, P2Y11 inhibitor, A2A Receptor inhibitor, A2B Receptor inhibitor, COX2 inhibitor, EP2 receptor antagonist, EP4 receptor antagonist, RON kinase inhibitor, ALK5 kinase inhibitor, CSF1 kinase inhibitor, PI3K delta kinase inhibitor, P13K gamma kinase inhibitor, BRAF V600E kinase inhibitor, arginase, and iNOS.

The immune modulating therapy may be radiotherapeutic immune stimulation selected from the group consisting of gamma irradiation, external beam radiotherapy, stereotactic radiotherapy, radiosurgery, virtual simulation, 3-dimensional conformal radiation therapy, intensity-modulated radiation therapy, intensity-modulated radiation therapy (IMRT), volumetric modulated arc therapy (VMAT), particle therapy, proton beam therapy, auger therapy, brachytherapy, intraoperative radiotherapy, radioisotope therapy, and beta irritation.

The immune modulating therapy may be a vaccine to TLR4 or TLR9. The vaccine may be toll-like receptor 4 (TLR4). The vaccine may be toll-like receptor 9 (TLR9).

The method may further comprise assessing whether a lymphatic system in a subject is dysregulated. Any method described herein may be used to assess the functioning of the lymphatic system.

D. Cancer

The cancer may be selected from the group consisting of lung cancer, breast cancer, a cancer of the gastrointestinal tract, a cancer of unknown origin, head and neck cancer, bladder cancer, prostate cancer, skin cancer, kidney cancer, a primary brain tumor, ocular tumor, sarcoma, a cancer of primary soft tissue, mesenchymal cancer, bone cancer, a tumor of the lymphatic system, and leukemia.

The cancer may be lung cancer selected from the group consisting of non-small cell lung cancer (NSCLC), squamous cell lung cancer, large cell lung cancer, small cell lung cancer, bronchogenic carcinoma, adenocarcinoma, neuroendocrine lung cancer, and bronchoalveolar lung cancer.

The cancer may be breast cancer selected from the group consisting of ductal carcinoma in situ (DCIS), invasive ductal carcinoma (IDC), lobular carcinoma (ILC), inflammatory breast cancer, lobular carcinoma in situ (LCIS), male breast cancer, Paget's disease of the nipple, and Phyllodes tumors of the breast. The breast cancer may be invasive ductal carcinoma selected from the group consisting of tubular carcinoma of the breast, medullary carcinoma of the breast, mucinous carcinoma of the breast, papillary carcinoma of the breast, and cribriform carcinoma of the breast. The cancer may be breast cancer defined by hormone receptor status selected from the group consisting of estrogen receptor positive, estrogen receptor negative, progesterone receptor positive, progesterone receptor negative, herceptin positive, herceptin negative, and combinations thereof. The cancer may be breast cancer defined by expression of a pred-defined set of genes selected from the group consisting of mammaprint, oncotypeDX, intrinsic subtypes, and nanostring prosigna.

The cancer may be a cancer of the gastrointestinal tract selected from the group consisting of a tumor of the stomach, gastric cancer, duodenal cancer, small or large intestine cancer, colorectal cancer, anal cancer, liver cancer, pancreatic cancer, gall bladder cancer, cholangiocarcinoma, and neuroendocrine cancer.

The cancer may be a skin cancer selected from the group consisting of basal cell cancer, squamous cell cancer, and melanoma.

The cancer may be kidney cancer selected from the group consisting of renal cell cancer and oncocytoma.

The cancer may be a primary brain tumor, selected from the group consisting of glioma, a tumor with gliomatous components, a tumor with neuronal components, a tumor with oligodendroglial components, oligodendroglioma, astrocytoma, and glioblastoma multiforme.

The cancer may be a tumor of the lymphatic system selected form the group consisting of B cell lymphoma, T cell lymphoma, diffuse B cell lymphoma, and Hodgkin's lymphoma.

The cancer may be leukemia selected from the group consisting of acute lymphoblastic leukemia, acute myeloid leukemia, chronic lymphocytic leukemia, and chronic myelogenous leukemia.

The cancer may be lung cancer and the method further may comprise administering one or more drugs selected from the group consisting of afatinib dimaleate, alectinib, bevacizumab, carboplatin, ceritinib, crizotinib, docetaxel, doxorubicin, erlotinib, etoposide, everolimus, gefitinib, gemcitabine, mechlorethamine, methotrexate, necitumumab, nivolumab, osimertinib, paclitaxel, paclitaxel albumin-stabilized nanoparticles, pembrolizumab, pemetrexed, ramucirumab, topotecan, vinorelbine, pharmaceutically acceptable salts thereof, and combinations thereof.

The cancer may be advanced cancer or metastatic cancer.

F. Chemotherapeutic Agents

The methods described herein may be conducted in combination with administering one or more chemotherapeutic agents. Non-limiting examples of chemotherapeutic compounds which can be used in combination treatments include, for example, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, campothecin, carboplatin, chlorambucil, cisplatin, cyclophosphamide, cytoxan, dactinomycin, daunorubicin, doxorubicin, epirubicin, hexamethyhnelameoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abcizimab; antimigratory agents; antisecretory agents (breveldin); immunosuppressives (cyclosporine, tacrolimus (FK-506), sirolimus (rapamycin), azathioprine, mycophenolate mofetil); antiangiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, campothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

The cancer may be lung cancer, such as non-small cell lung cancer (NSCLC). Suitable drugs for treated non-small cell lung cancer include, but are not limited to, Abitrexate™ (methotrexate), Abraxane™ (paclitaxel albumin-stabilized nanoparticles), Afinitor™ (everolimus), Alecensa™ (alectinib), Alimta™ (pemetrexed disodium), Avastin™ (bevacizumab), Cyramza™ (ramucirumab), Folex™ (methotrexate), Gilotrif™ (afatinib dimaleate), Gemzar™ (gemcitabine hydrochloride), Iressa™ (gefitinib), Keytruda™ (pembrolizumab), Mexate™ (methotrexate), Mustargen™ (mechlorethamine hydrochloride), Navelbine™ (vinorelbine tartrate), Opdivo™ (nivolumab), Paraplat™ (carboplatin), Paraplatin™ (carboplatin), Portrazza™ (necitumumab), Tagrisso™, (osimertinib), Tarceva™ (erlotinib hydrochloride), Taxol™ (paclitaxel), Taxotere™ (docetaxel), Xalkori™ (crizotinib), and Zykadia™ (ceritinib). Suitable drug combinations for treating non-small cell lung cancer include, but are not limited to, carboplatin and taxol, and gemcitabine and cisplatin.

Suitable drugs for treating small cell lung cancer include, but are not limited to, Abitrexate™ (methotrexate), Afinitor™ (everolimus), doxorubicin hydrochloride, Etopophos™ (etoposide phosphate), etoposide, Folex™ (methotrexate), Hycamtin™ (topotecan hydrochloride), Mexate™ (methotrexate), and Mustargen™ mechlorethamine hydrochloride).

Pharmaceutical compounds that can be used in combination with a VEGFR-3 and a cancer immune modulating therapy such as an immune checkpoint inhibitor and (0) VEGFR-2 antagonist: (1) inhibitors of release of "angiogenic molecules," such as bfGF (basic fibroblast growth factor); (2) neutralizers of angiogenic molecules, such as an anti-ObHGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin D3 analogs, alpha interferon, and the like.

G. Angiogenesis Inhibitors

The methods described herein may be conducted in combination with administering one or more angiogenesis inhibitors. Compounds that inhibit angiogenesis include for example endostatin protein or derivatives, lysine binding fragments of angiostatin, melanin or melanin-promoting compounds, plasminogen fragments (e.g., Kringles 1-3 of plasminogen), tropoin subunits, antagonists of vitronectin, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors.

Depending on the combinatory therapy, administration of the polypeptide therapeutic agents may be continued while the other therapy is administered and/or thereafter. Administration of the therapeutic agents can be made in a single dose, or in multiple doses. In some instances, administration of the therapeutic agents can begin at least several days prior to the conventional therapy, while in other instances, administration can begin either immediately before or at the time of the administration of the conventional therapy.

Although the disclosure described herein is susceptible to various modifications and alternative iterations, specific embodiments thereof have been described in greater detail above. It should be understood, however, that the detailed description of the composition is not intended to limit the disclosure to the specific embodiments disclosed. Rather, the disclosure is intended to cover all modifications, equivalents, and alternatives falling within the spirit and scope of the disclosure as defined by the claim language.

Definitions

The compounds described herein have asymmetric centers. Compounds of the present disclosure having an asymmetrically substituted atom may be isolated in optically active or racemic form. All chiral, diastereomeric, racemic forms and all geometric isomeric forms of a structure are intended, unless the specific stereochemistry or isomeric form is specifically indicated.

"Inhibiting an established tumor metastasis" refers to decreasing the size and/or rate of growth of a metastasis which has been already established. Established metastases include metastases in lymph nodes (regional metastases) and distant organs (systemic metastases).

"Lymphangiogenesis" refers to growth of new lymphatic vessels.

"Therapeutically effective" applied to dose or amount refers to that quantity of a pharmaceutical composition sufficient to result in a desired therapeutic activity upon administration to a subject in need thereof, or sufficient to reduce or eliminate at least one symptom of the disease being treated.

"Subject" means any animal, including mammals. The term may refer to a human, a non-human primate, a bovine, an ovine, an equine, a porcine, a canine, a feline, or a rodent (mouse or rat).

When introducing elements of the present disclosure or the embodiments(s) thereof, the articles "a," "an," "the," and "said" are intended to mean that there are one or more of the elements. The terms "comprising," "including," and "having" are intended to be inclusive and mean that there may be other elements other than the listed elements.

Having described the disclosure in detail, it will be apparent that modifications and variations are possible without departing from the scope of the disclosure defined in the appended claims.

EXAMPLES

The following examples are included to show certain embodiments of the disclosure. It should be appreciated by those of skill in the art that the techniques disclosed in the examples represent techniques discovered by the inventors to function well in the practice of the disclosure. Those of skill in the art should, however, considering the present disclosure, appreciate that many changes can be made in the specific embodiments disclosed and still obtain a like or similar result without departing from the spirit and scope of the disclosure, therefore all matter set forth is to be interpreted as illustrative and not in a limiting sense.

Example 1—Evaluation of Dysregulated Lymphatic System in Lung Cancer Patients Treated with PD-1 Inhibitor Immunotherapy Patients with advanced or metastatic lung cancer were treated with an inhibitor of PD-1. Their lymphatic systems are evaluated for dysfunction. In one instance, lymphatic system evaluation was performed with serum measurements of VEGF C, VEGF D, or midkine in patients before starting therapy or during treatment. In other instances, the dysfunction was measured with pretreatment imaging studies and/or similar imaging across treatment with immunotherapy therapy, including either computed tomography, MRI, and nuclear medicine tests including PET imaging or ventilation perfusion scans.

Patients with dysregulated lymphatic systems ("biomarker positive") did significantly worse across the objective measures of response based on progression free survival, overall survival, durable response, and objective response as found by Response Evaluation Criteria in Solid Tumors (RECIST 1.1) and by immune-related response criteria (irRC).

Only patients with measurable disease at baseline were included in protocols where objective tumor response was the primary endpoint. "Measurable disease" was the presence of at least one measurable lesion. If the measurable disease was restricted to a solitary lesion, neoplasticity was confirmed by cytology/histology. Measurable lesions could be measured in at least one dimension with longest diameter about 20 mm using conventional techniques or about 10 mm with spiral CT scan. Non-measurable lesions, included small lesions (longest diameter <20 mm with conventional techniques or <10 mm with spiral CT scan), bone lesions, leptomeningeal disease, ascites, pleural/pericardial effusion, inflammatory breast disease, lymphangitis cutis/pulmonitis, cystic lesions, and abdominal masses not confirmed or followed by imaging techniques. All baseline evaluations were performed as closely as possible to the beginning of treatment and not more than 4 weeks before the beginning of the treatment. The same method of assessment and the same technique characterized each reported lesion at baseline and during follow-up.

Conventional CT and MRI were performed with cuts of 10 mm or less in slice thickness contiguously. Spiral CT were performed using a 5-mm contiguous reconstruction algorithm. his applied to tumors of the chest, abdomen and pelvis. Head and neck tumors and those of extremities followed specific protocols. Lesions on chest X-ray were acceptable as measurable lesions when they defined and surrounded by aerated lung.

Tumor markers alone could not assess response. If markers were initially above the upper normal limit, they must normalize for a patient to be in complete clinical response when all lesions disappeared. Cytology and histology differentiated between partial and complete responses. Target lesions were selected based on size (lesions with the longest diameter) and suitability for exact repeated measurements (either by imaging techniques or clinically). A sum of the longest diameter (LD) for all target lesions was calculated and reported as the baseline sum LD. The baseline sum LD was the reference by which the objective tumor was characterized. Other lesions (or sites of disease) were identified as non-target lesions and recorded at baseline. Measurements of these lesions are not needed, but the presence or absence of each were noted throughout follow-up.

"Complete Response" (CR) was the disappearance of all target lesions, or the disappearance of all non-target lesions and normalization of tumor marker level.

"Partial Response" (PR) was at least a 30% decrease in the sum of the longest diameter of target lesions, referring to the baseline sum longest diameter.

"Progressive Disease" (PD) was at least a 20% increase in the sum of the longest diameter of target lesions, referring to the smallest sum longest diameter recorded since starting treatment or one or more new lesions appeared. PD is also appearance of one or more new lesions and/or unequivocal progression of existing non-target lesions.

"Incomplete Response" or "Stable Disease" (SD) had neither sufficient shrinkage to qualify for PR nor sufficient increase to qualify for PD, referring to the smallest sum LD since the treatment started. SD had persistence of one or more non-target lesions and/or maintenance of tumor marker level above the normal limits.

Although progression of only "non-target" lesions was exceptional, in such circumstances the opinion of the treating physician prevailed and the review panel or the study chair later confirmed the progression status. The best overall response was the best response recorded from the start of the treatment until disease progression/recurrence, referring to PD for the smallest measurements recorded since the treatment started. The patient's best response assignment depends on achieving both measurement and confirmation criteria, as shown in Table 1.

TABLE 1

Response measurements

| Target lesions | Non-Target lesions | New Lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or No | PD |
| Any | PD | Yes or No | PD |
| Any | Any | Yes | PD |

Patients with a global deterioration of health status needing discontinuation of treatment without objective evidence of disease progression were classified as having "symptomatic deterioration." Objective progression was documented even after discontinuation of treatment. In some circumstances, it was difficult to distinguish residual disease from normal tissue. When the evaluation of complete response depended on this determination, the residual lesion was investigated using a fine needle aspirate or biopsy to confirm the complete response status. Confirmation of objective response avoided overestimating the response rate seen. Where confirming the response was not feasible, the response reports stated such.

To be assigned a status of PR or CR, changes in tumor measurements were confirmed by repeat assessments no less than 4 weeks after the criteria for response were first met. Longer intervals from the study protocol were also proper. For SD, follow-up measurements met the SD criteria at least once after study entry at a minimum interval (in general, not less than 6-8 weeks) defined in the study protocol. The duration of overall response was measured from the time measurement criteria were met for CR or PR, whichever status was first recorded, until the first date that recurrence or PD was objectively documented, referring to PD for the smallest measurements recorded since the treatment started.

SD was measured from the start of the treatment until the criteria for disease progression were met, referring to the smallest measurements recorded since the treatment started. The clinical relevance of the duration of SD varied for different tumor types and grades. Therefore, it was highly recommended that the protocol specified the minimal time interval between two measurements for determining SD. This time interval considered the expected clinical benefit such a status brought to the studied population.

For trials where the response rate was the primary endpoint, all responses were reviewed by an independent expert at the study's completion, including simultaneous review of the patients' files and radiological images.

All patients included in the study were assessed for response to treatment, even if treatment majorly deviated from protocol or if they were ineligible. Each patient was assigned to (1) complete response, (2) partial response, (3) stable disease, (4) progressive disease, (5) early death from malignant disease, (6) early death from toxicity, (7) early death because of other cause, or (9) unknown (not assessable, insufficient data). All patients who met the eligibility criteria were included in the main analysis of the response rate. Patients in response categories 4-9 should failed to respond to treatment (disease progression). Thus, an incorrect treatment schedule or drug administration did not exclude them from the analysis of the response rate. Precise definitions for categories 4-9 were protocol specific.

Conclusions were based on all eligible patients. Analyses of a subset of patients, excluded those with major protocol deviations, such as early death for other reasons, early discontinuation of treatment, major protocol violations, etc. However, conclusion for treatment efficacy were not drawn from the analyses of subsets. The reasons for excluding patients from the analysis were reported. Moreover, the 95% confidence intervals were provided.

Figure 3:
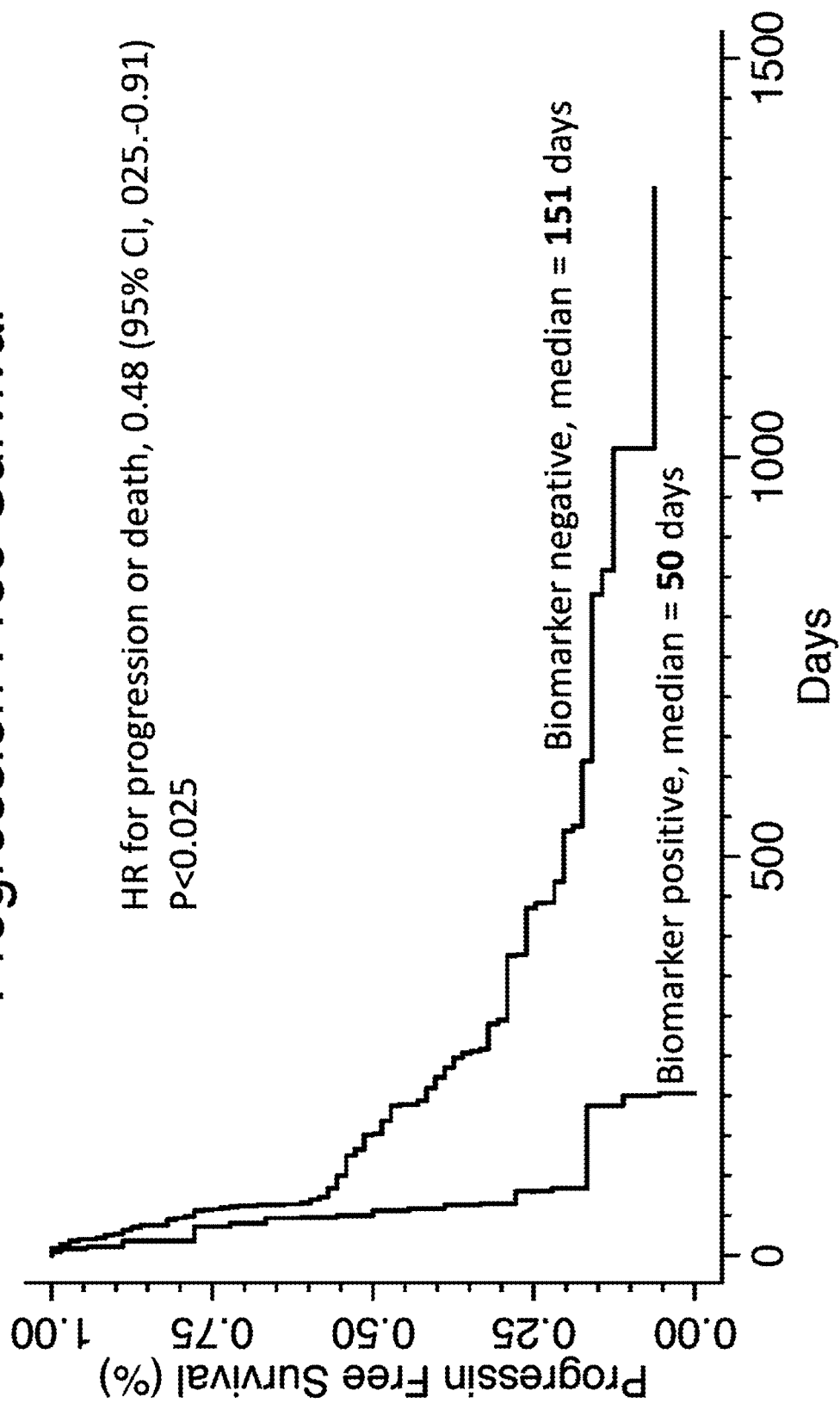
FIG. 3 shows progression free survival (%) as a function of time in days for cancer treatment using immune modifying therapy. Biomarker positive patients had a median survival of 50 days. Biomarker negative patients had a median survival of 151 days. HR for progression or death was 0.48 (95% CI, 025.-0.91), at P<0.025.

FIG. 3 shows progression free survival (%) as a function of time in days for cancer treatment using immune modifying therapy. Biomarker positive patients had a median survival of 50 days. Biomarker negative patients had a median survival of 151 days. HR for progression or death was 0.48 (95% CI, 025.-0.91), at P<0.025. Table 2 shows the Cox proportional hazard mode progression free survival for patient subsets, including age, race, dosing, smoking status, type of lung cancer, EGFR mutation, or prior systemic therapies. Table 2 report the hazard ratio, standard deviation, z value, p value related to the absolute value of z, and the 95% confidence interval.

Table 2: Cox Proportional Hazard Mode Progression Free Survival (PFS)

```
Log likelihood = -281.59881          Prob > chi2 = 0.0468
```

| _t | Haz. Ratio | Std. Err. | z | P>|z| | [95% Conf. Interval] | |
|---|---|---|---|---|---|---|
| ▓▓▓▓▓▓▓▓▓▓▓▓▓▓▓▓▓▓ | 2.092233 | .6869697 | 2.25 | 0.025 | 1.09932 | 3.981952 |
| age651 | 1.026221 | .2587925 | 0.10 | 0.918 | .6260152 | 1.682275 |
| racewhite1asian2hispanic3 | .9691919 | .1316666 | -0.23 | 0.818 | .7426299 | 1.264874 |
| dosingq321q3102q2103 | .873988 | .1517212 | -0.78 | 0.438 | .6219277 | 1.228286 |
| SmokingStatuspositiveorform | .6987349 | .1975865 | -1.27 | 0.205 | .4014319 | 1.216222 |
| TypeofLungCanceradenocompo | 1.438827 | .4424634 | 1.18 | 0.237 | .7874985 | 2.628859 |
| EGFRmt1mutant | 1.190704 | .3369266 | 0.62 | 0.537 | .6838242 | 2.073386 |
| priorsystemictherapies1 | .9473828 | .2945776 | -0.17 | 0.862 | .5150558 | 1.742596 |

Figure 4:
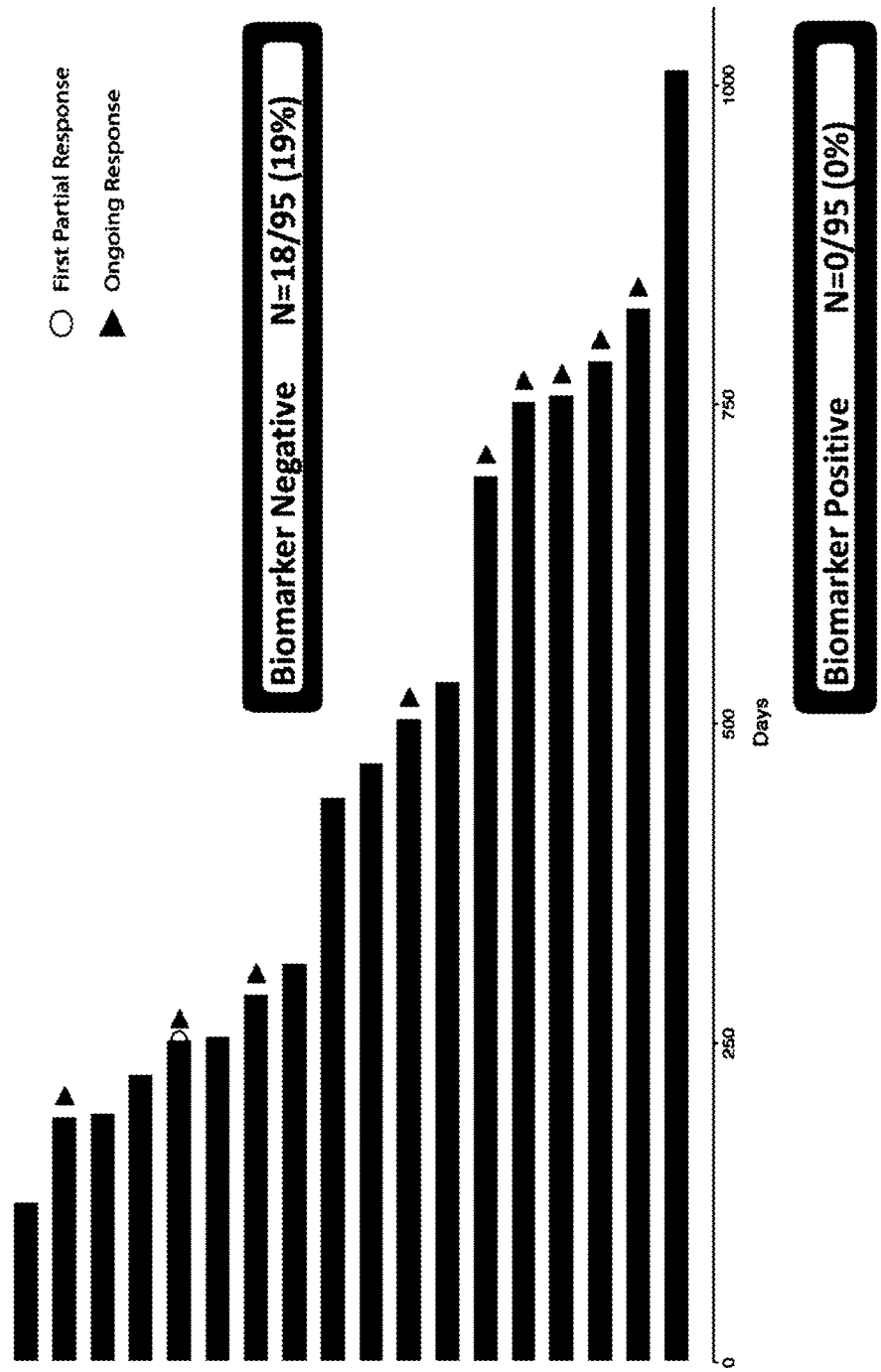
FIG. 4 shows the objective response of partial responses or complete responses (PR/CR). The first partial responses were denoted by ellipses. The solid triangles show ongoing responses. Biomarker negative patients had an N=18/95 (19%). Biomarker Positive patients had an N=0/95 (0%).

FIG. 4 shows the objective response of partial responses or complete responses (PR/CR). The first partial responses were denoted by ellipses. The solid triangles show ongoing responses. Biomarker negative patients had an N=18/95 (19%). Biomarker Positive patients had an N=0/95 (0%).

Figure 5:
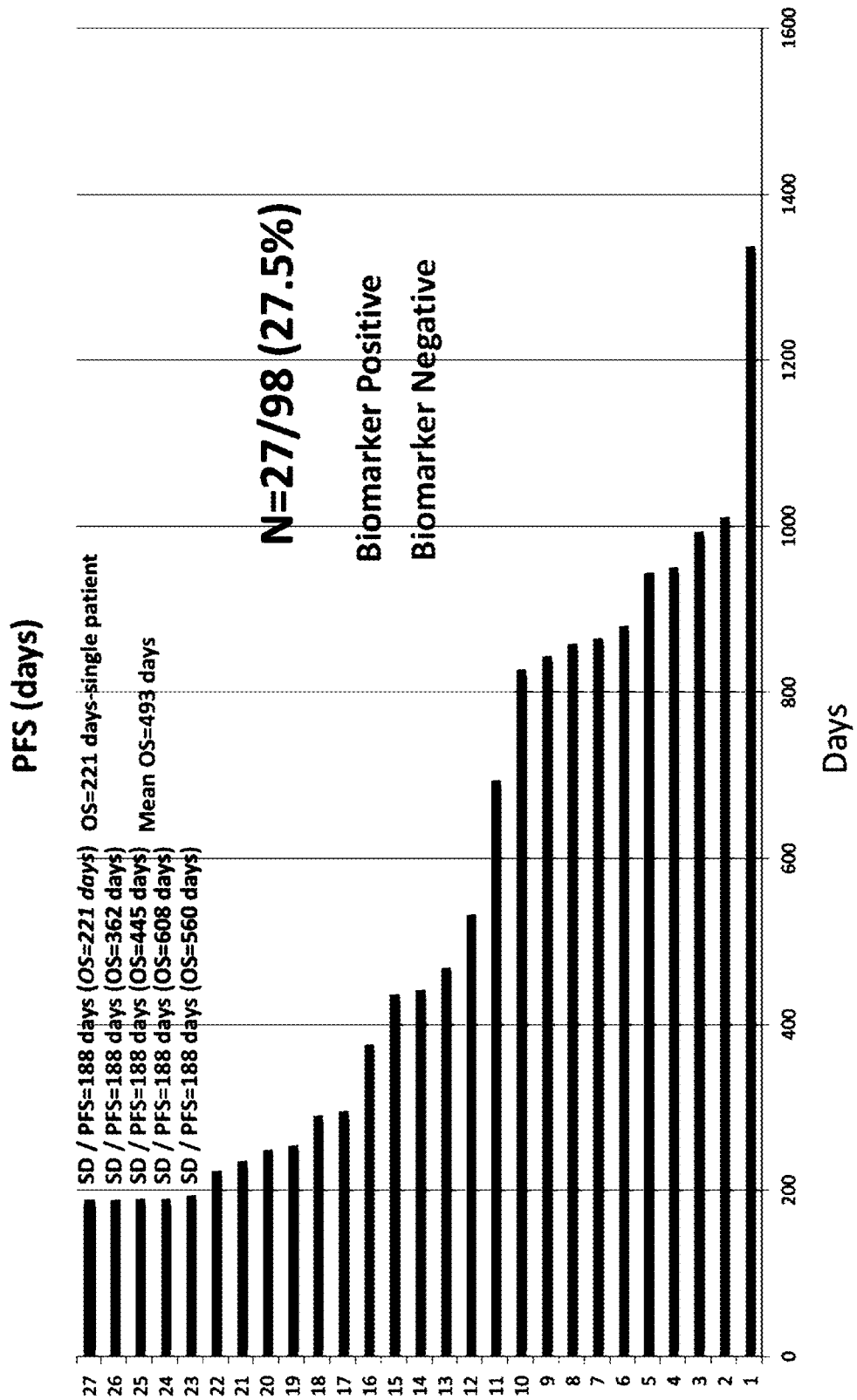
FIG. 5 shows the durable clinical response for the stable disease (SD) or partial response (PR) lasting at least 180 days. Lines 1-26 were biomarker negative patients. Line 27 was a biomarker positive patient.

FIG. 5 shows the durable clinical response for the stable disease (SD) or partial response (PR) lasting at least 180 days. Lines 1-26 were biomarker negative patients. Line 27 was a biomarker positive patient.

As seen from the data presented above, patients without a dysregulated lymphatic system had a strikingly significant improvement in survival, thus confirming lymphatic system status for deciding treatment response in cancer patients treated with immune modulating therapies. Further, statistical analysis showed that a dysregulated lymphatic system in this cohort was the single strongest factor for predicting response. The dysregulated lymphatic system outweighed other known important prognostic and predictive factors, including age, race, immunotherapy dosing, total tumor burden, gender, smoking and mutation status, and lung cancer cell type. (See especially Table 2.)

Example 2—Treatment of Advanced and Metastatic Lung and Breast Cancers with Modulators of Lymphatic Biology Plus Immunotherapy Results in Improved Outcomes One to two million cells of either LLC lung cancer or 4T1 breast cancer cells are subcutaneously implanted into syngeneic mice (C57 Black 6 and BALB/c). Animals are treated with vehicle alone as a control, with chemotherapy (cisplatin), or with immunotherapy alone (anti-PD-1 mAb). Animals are imaged by intravascular ultrasound (IVUS), CT/PET, or MRI, for growth of the primary tumor and for metastatic spread of tumor. Blood samples are obtained for multiplexed measure of serum biomarkers of lymphatic biology function (Millipore mouse 24 plex; MAGPMAG-24K). Around Study Day 10, animals are injected with 1-1.5 million more tumor cells into the tail vein. Between Study Days 13 and 16, the primary tumor is surgically resected and animals resume treatment.

Treatment groups include (1) anti-PD-1 mAb alone; (2) anti-PD-1-mAb plus lymphatic system modulator (anti-VEGF C or anti-VEGF R3 mAb, or SAR131675); (3) cisplatin alone; (4) lymphatic system modulator (anti-VEGF C or anti-VEGF R3 mAb, or SAR131675) plus cisplatin; and (5) negative control (no treatment).

Animals are imaged weekly and blood for serum multiplex measurements continued and evaluated. Survival studies and analysis are performed and animals are evaluated based on overall survival, progression free survival, objective and durable response, and serum biomarker measurements. Lung tissue, lymphatics and reginal lymph nodes, and tumor tissue are concurrently evaluated upon animal sacrifice for functional immune evaluation and analysis of the tumor and disease analysis.

Results show that animals do not respond to anti-PD-1, and show no to marginal response to cisplatin. This effect is more pronounced in those groups with dysregulated lymphatic systems as measured by the imaging tests and serum biomarkers tests. However, adding a lymphatic system modulator to either the anti-PD-1 mAb or the cisplatin-treated groups results in marked significant improvement. Measured outcomes include progression free survival, objective and durable responses, and improvement in biomarker profiles.

Tumor growth is augmented in non-lymphatic system modulator treated mice, compared to mice treated with a lymphatic system modulator combination. Expression of inflammatory cytokines such as IFN-γ, TNF-α, IL-2, and IL-10 in draining lymph nodes is significantly reduced in non-lymphatic modulator treated mice. Moreover, decreased levels of tumor-associated antigens are detected in draining lymph nodes in these mice, together with impaired antigen presentation. CD8+ T cells in draining lymph nodes derived from non-lymphatic system modulator treated mice also show significantly decreased cytotoxic activity in vitro. Finally, tumor suppression activity of CD8+ T cells derived from non-lymphatic system modulator treated mice was reduced when adoptively transferred to naive wild-type mice.

In contrast, the reverse is seen in lymphatic system modulator treated mice with restoration or augmentation of immune response and antigen presentation and immune cell priming. IFN-γ enzyme-linked ImmunoSpot (ELISAPOT) assay, which enables direct quantification of immune responses, similarly show decreased activity. Similar findings are seen with myeloid derives suppressor cells, T regulatory cells and inhibitory macrophages (M2) which are increased in the tumor and lymph nodes and a decreased seen in antigen presenting cells (e.g. cross-presenting CD8+ T cells, and dendritic cells and M1 cells in the supporting and draining lymph nodes) in the nonlymphatic modulating system treated mice that also have worse outcomes. Additionally, lymphatic vessels show increased expression of PD-1, and blocking PDL1 with lymphatic system modulators results in increased T-cell stimulation by antigen-presenting lymphatic endothelial cells (LECs) in vitro overcoming peripheral, tumor-associated lymphatic endothelium associated T-cell inhibition.

These findings support that lymphatic transport is essential in generating optimal tumor-specific immune responses mediated by CD8+ T cells. Lymphatic transport is impaired in subjects with dysfunctional lymphatic systems. Concurrent treatment with a lymphatic modulator (e.g. SAR131675, or anti-VEGF-C, or Anti-VEGF R3 m AB) and either an immune modulator (e.g. checkpoint inhibitor) or chemotherapy (e.g. cisplatin), can overcome this inhibition and results in functional immunological improvements.

Although animals treated with lymphatic modulator improve regardless of treatment (such as with the concurrent treatment with immunotherapy or with cisplatin), the degree of improvement across objective measures directly correlates with underlying lymphatic dysfunction. These results therefore confirm that lymphatic modulating agents have a profound synergistic effect with immunotherapy and/or chemotherapy in syngeneic animal models, where these drugs alone have little to no effect by themselves. Further, this effect is mechanistically related to priming and facilitation of the immune system and/or overcoming immune barriers associated with or aided by the tumor.

Example 3

Treatment with lymphatic system modulators with immune-modulators or chemotherapy significantly improves objective outcomes in mice with advanced or metastatic cancer with dysregulated lymphatic systems and prevents the progression to lymphatic carcinomatosis, a form of severe lymphatic dysregulation in subjects with cancer.

The experiments from Example 2 are performed using the same animal models (4T1 and LLC) in syngeneic mice.

Another group of tumor cells are transfected to overexpress VEGF-C to stimulate severe lymphatic dysregulation. Overexpression of VEGF C by tumor cells can result in a severe lymphatic dysregulation and an extremely aggressive lymphangitic carcinomatosis, which is a subset of the groups of dysregulated lymphatic disorders resistant to immunotherapy (Example 1). When treated with a lymphatic system modulator, outcomes are profoundly improved in both objective and immune/functional (Example 2). In this experiment, it is evaluated whether advanced tumors with inherent lymphatic dysregulation, or with exaggerated lymphatic dysregulation driven by VEGF C hyperexpression, can be treated, and whether treatment can prevent mice with cancers from progressing to severe lymphangitic carcinomatosis.

Treatment groups include (1) anti-PD-1 mAb alone; (2) anti-PD-1-mAb plus lymphatic system modulator (anti-VEGF C or anti-VEGF R3 mAb, or SAR131675); (3) cisplatin alone; (4) lymphatic system modulator (anti-VEGF C or anti-VEGF R3 mAb, or SAR131675) plus cisplatin; and (5) negative control (no treatment).

All mice, especially mice (both 4T1 and LLC) with dysregulated lymphatic systems as measured by imaging, and functional assays, are highly and significantly responsive to lymphatic system modulators plus immune-modulator or chemotherapy, both functionally and by objective measures. (These are similar objective measures as those described in Example 2.) This finding is more pronounced in the VEGF-C overexpressing animal models with exaggerated lymphatic dysfunction and in those with lymphatic carcinomatosis. Animals with lymphangitic carcinomatosis also improve in imaging and functional measurements (Example 2), when treated with a lymphatic system modulator plus either immunomodulatory or chemotherapy. This therapy can potentially treat and overcome this highly aggressive form of advanced cancer.

Further, preventative treatment with a lymphatic system modulator alone (SAR131675, anti-VEGF-C or anti-VEGF R3) or with an immune modulator or chemotherapy significantly improves objective and functional outcomes in these animals. The treatment prevents development of further dysregulated lymphatic dysfunction, such that no mouse progresses to lymphangitic carcinomatosis. These studies show that lymphatic system modulators with immune modulators or chemotherapy treated aggressive tumors, some of which had lymphatic dysfunction and aggressive lymphangitic carcinomatosis, and prevents the progression and development of lymphatic carcinomatosis.

Example 4

In examining a subset of patients from Example 1, tumors responded to checkpoint inhibition based upon lymphatic dysfunction, independent of PD-1/L1, DNA mismatch repair status, microsatellite instability status, or hypermutant status/tumor neoantigen burden.

Patients with advanced or metastatic lung cancer were treated with an inhibitor of PD-1. Patients with a low or negative PD-L1 tumor proportion score (TPS) were evaluated as specified by the drug label, and thus not indicated for the drug and not expected to respond. Their lymphatic systems were evaluated for the dysfunction. In one instance, lymphatic system evaluation was performed with serum measurements of VEGF C, VEGF D or heparin-binding factor midkine in patients before therapy or during treatment. In other instances, the dysfunction was measured with pre-treatment imaging studies and/or similar imaging across treatment with immunotherapy therapy, including computed tomography, MRI, and nuclear medicine tests including PET imaging or ventilation perfusion scan.

Evaluating objective measures of response in these patients based on progression free survival, overall survival and durable and objective response (RECIST 1.1) and by immune-related response criteria (irRC) confirmed that patients with dysregulated lymphatic systems (designated as "Biomarker Positive" groups) did significantly worse across all these objective measures (overall survival, progression free survival, objective response, and durable clinical response).

Keytruda™ product label teaches to the contrary. Pembrolizumab (formerly MK-3475 and lambrolizumab, trade name Keytruda™) is a humanized antibody used in cancer immunotherapy. It blocks a protective mechanism on cancer cells, and allows the immune system to destroy those cancer cells. It targets the programmed cell death 1 (PD-1) receptor. It is indicated for patients with metastatic NSCLC, whose tumors have high PD-L1 expression with a tumor proportion score (TPS) of at least 50%, as determined by an FDA-approved test, with no epidermal growth factor receptor (EGFR) or anaplastic lymphoma kinase (ALK). Keytruda™ is also indicated for patients with metastatic NSCLC, whose tumors express PD-L1 (TPS of at least 1%), as determined by an FDA-approved test, with disease progress on or after platinum-containing chemotherapy. That is, the art teaches that patients with low PD-L1 levels cannot be treated.

Opdivo™ is a programmed death receptor-1 (PD-1) blocking antibody. Also known as, nivolumab is indicated for adult and pediatric (12 years and older) patients with microsatellite instability-high (MSI-H) or mismatch repair deficient (dMMR) metastatic colorectal cancer that has progressed following treatment with a fluoropyrimidine, oxaliplatin, and irinotecan. Again, the art teaches that patients with low PD-L1 levels cannot be treated.

However, contrary to teaching in the art, patients without a dysregulated lymphatic system, yet who were not expected to respond based on their PD-L1 TPS, had a striking response to the therapy with significant duration of overall and progression free survival, thus confirming that the lymphatic system critically determined response to immune checkpoint therapy.

Further, statistical analysis showed that the presence of a dysregulated lymphatic system in this cohort was the single strongest factor for predicting response, outweighing other known important prognostic and predictive factors including age, race, immunotherapy dosing, total tumor burden, gender, smoking and mutation status, and lung cancer cell type. Similar results were seen in patients with treated with PD-L1 inhibitors, with low neoantigen burdens, hypermutant status, and the tumor types shown not to respond to checkpoint inhibition therapy described above.

Figure 6:
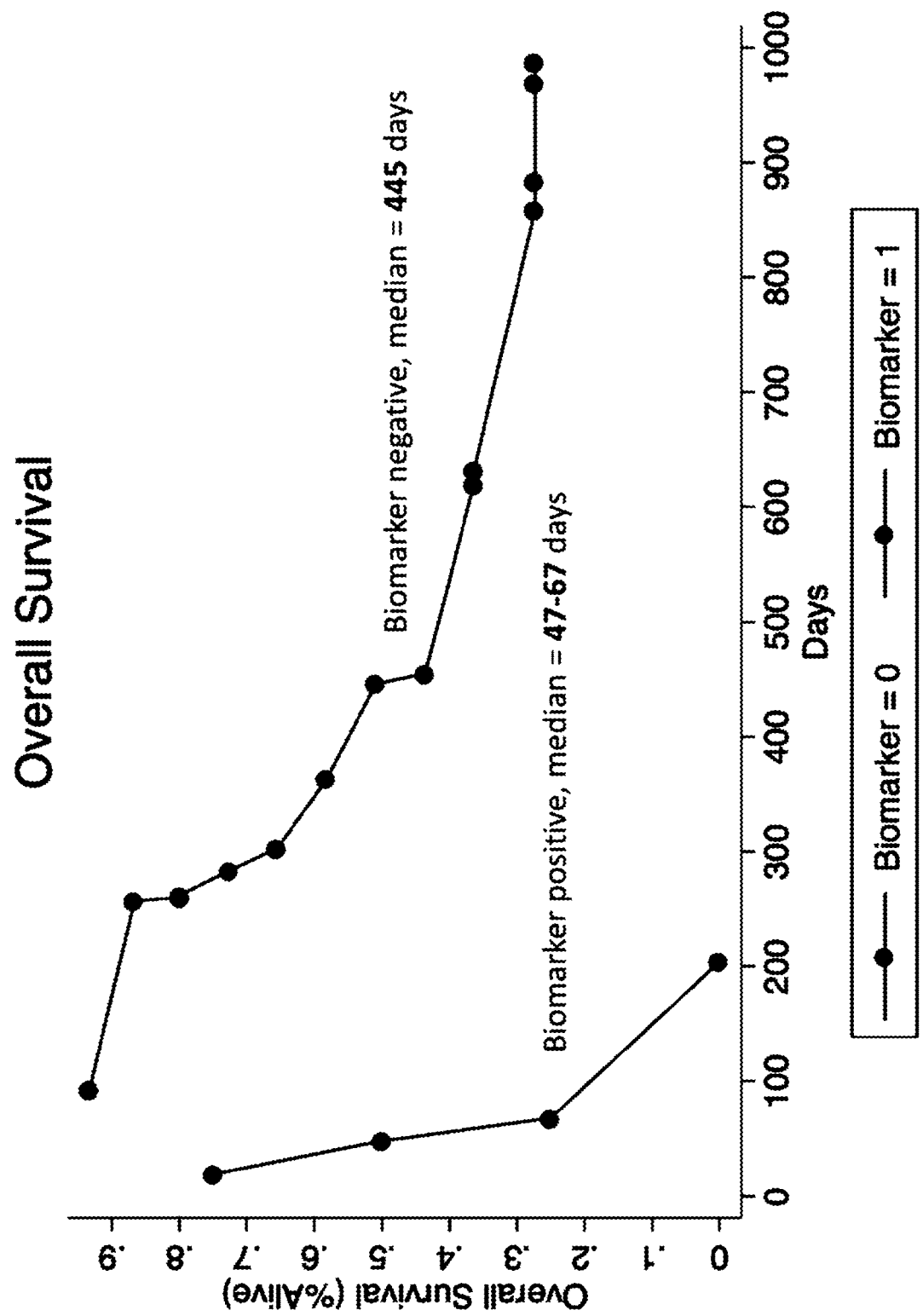
FIG. 6 shows overall survival (% alive) as a function of time in days. Biomarker positive patients survived a median of 47 to 67 days. Biomarker negative patients survived a median of 445 days.

FIG. 6 shows overall survival (% alive) as a function of time in days. Biomarker positive patients survived a median of 47 to 67 days. Biomarker negative patients survived a median of 445 days.

Figure 7:
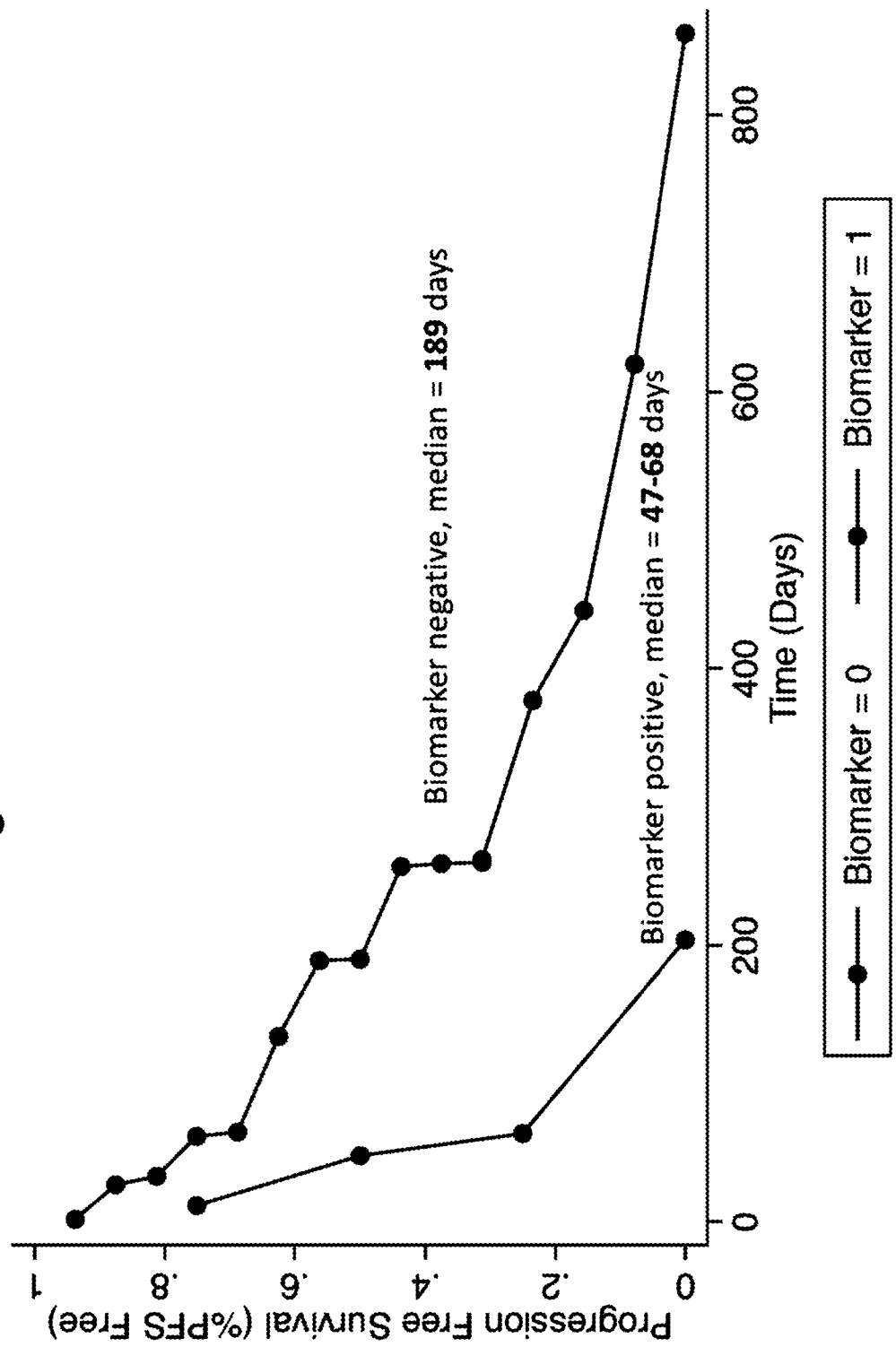
FIG. 7 shows progression free survival (%) as a function of time in days. Biomarker positive patients had a median survival of 47 to 68 days. Biomarker negative patients had a median survival of 189 days.

FIG. 7 shows progression free survival (%) as a function of time in days. Biomarker positive patients had a median survival of 47 to 68 days. Biomarker negative patients had a median survival of 189 days.

Thus, dysregulated lymphatic systems were a powerful predictor of response to immune-modulating therapies independent of the art which teaches that PD-L1/PD-1 TPS and hypermutant/neoantigen status were critical determinants of response. Certain tumors types, such as triple negative breast cancer, colon, pancreatic, glioblastoma multiforme (GBM), prostate cancer, inflammatory, and ER+/HER2+ breast cancers, did not respond well to these therapies.

Example 5—Specificity of Monoclonal Antibodies Against Flt4

The purified recombinant Fms-related tyrosine kinase 4 (Flt4) extracellular domain-6×His fusion product was labelled with europium according to Mukkala et al., *Anal. Biochem*, 176(2):319-325 (1989), with the following modification: a 250 times molar excess of isothiocyanate OTTA-Eu (N1 chelate, WALLAC, Finland) was added to the Flt4 solution (0.5 mg/ml in PBS) and the pH was adjusted to about 9 by adding 0.5 M sodium carbonate buffer, pH 9.8. The labelling was performed overnight at +4° C. Unbound label was removed using PD-10 (Pharmacia, Sweden) with TSA buffer (50 mM Tris-HCl, pH 7.8, containing 0.15 M NaCl) as eluent.

After purification, 1 mg/mL bovine serum albumin (BSA) was added to the labelled Flt4 and the label was stored at +4° C. The average number of europium ions incorporated per Flt4 molecule was 1.9, as determined by measuring the fluorescence in a ratio to that of known EuCl3 standards (Hemmila et al., *Anal. Biochem.*, 137:335-343 (1984)).

The antibodies were screened using a Sandwich-type immunofluorometric assay, using microtitration strip wells (NUNC, polysorb) coated with rabbit anti-mouse Ig (Z 259, DAKOPATTS). The pre-coated wells were washed once by Platewash 1296-024 (WALLAC) with DELFIA wash solution. The DELFIA assay buffer was used as a dilution buffer for cell culture supernatants and for serum of the splenectomized mouse (at dilutions between 1:1000 to 1:100,000) used as positive control in the preliminary screening assay. An overnight incubation at +4° C. (or alternatively for 2 hours at room temperature) was begun by shaking on a Plateshake shaker (1296-001, WALLAC) for 5 minutes followed by washing four times with wash solution as described above.

The europium-labelled Flt4 was added at a dilution of 1:500 in 100 mL of the assay buffer. After 5 minutes on a Plateshake shaker and one-hour incubation at room temperature, the strips were washed as described above.

Enhancement solution (DELFIA) was added at 200 μL/well. The plates were then shaken for 5 minutes on a Plateshake shaker and the intensity of fluorescence was measured by ARCUS-1230 (WALLAC) for 10-15 minutes. (Lovgren et al., In: Collins W. P. (Ed.) *Alternative immunoassays*, John Wiley & Sons Ltd. (1985), pp. 203-216). The DELFIA results show that all monoclonal antibodies tested bound the Flt4 EC antigen.

Monoclonal antibodies reactive with the Flt4 (and the hybridomas which produce the antibodies) were selected for further screening. The resulting monoclonal antibodies were used in double antibody immunofluorescence staining of NIH3T3 cells expressing the LTR-FLT41 construct and neomycin-resistant transfected NIH3T3 cells: The cells were detached from the culture plates using EDTA, stained, and analyzed in a fluorescence-activated cell sorter (FACS). The results of FACS analysis are given as percentages of cells staining positive with the indicated monoclonal antibody.

The FACS results with LTR-FLT41-transfected cells indicate that the antibodies effectively recognize Flt4-expressing cells. These same antibodies give only background staining of neomycin phosphotransferase-transfected NIH3T3 cells. Thus, the antibodies specifically recognize the Flt4 tyrosine kinase on the cell surface.

One clone, designated anti-Flt4 hybridoma 9D9F9, was found to stably secrete monoclonal antibody which was determined to be of immunoglobulin class IgG1 by immunofluorometric assay (IFMA). Hybridoma 9D9F9 was deposited with the Leibniz Institute, DSMZ-German Collection of Microorganisms and Cell Cultures GmbH, InhoffenstraBe 7B, 38124 Braunschweig, Germany, Mar. 23, 1995, and given accession No. ACC 2210. Methods for selecting another antibody that competes for binding to the same epitope bound by a monoclonal antibody are well-established in the art, for example see Robert C. Ladner (2007) "Mapping the Epitopes of Antibodies," *Biotechnology and Genetic Engineering Reviews*, 24:1, 1-30.

While specific embodiments have been described above regarding the disclosed embodiments and examples, such embodiments are only illustrative and do not limit the scope of the disclosure. Changes and modifications can be made following ordinary skill in the art without departing from the disclosure in its broader aspects as defined in the following claims.

What is claimed is:

1. A method to treat cancer in a subject in need of inhibition of lymphangiogenesis, comprising:
   a. assessing whether the lymphatic system in the subject is dysregulated;
   b. administering to the subject a therapeutically effective amount of a first monoclonal antibody chosen from pembrolizumab, nivolumab, or a combination thereof, thereby inducing an immune modifying effect in the subject; and
   c. further administering to the subject a therapeutically effective amount of a second monoclonal antibody, before or concurrent with the administration of the first monoclonal antibody, wherein the second monoclonal antibody binds to the extracellular domain of VEGFR-3, and wherein the second monoclonal antibody inhibits the lymphangiogenesis in the subject.

2. A method to treat cancer in a subject in need of inhibition of lymphangiogenesis, comprising:
   a. selecting a subject with a condition of a dysregulated lymphatic system comprising lymphangiogenesis;
   b. administering to the subject a therapeutically effective amount of a first monoclonal antibody chosen from pembrolizumab, nivolumab, or a combination thereof, thereby inducing an immune modifying effect in the subject; and
   c. further administering to the subject a therapeutically effective amount of a second monoclonal antibody, before or concurrent with the administration of the first monoclonal antibody, wherein the second monoclonal antibody binds to the extracellular domain of VEGFR-3, and wherein the second monoclonal antibody inhibits the lymphangiogenesis in the subject.

3. The method of claim 2, wherein the second monoclonal antibody is a chimeric or humanized antibody.

4. The method of claim 2, wherein the second monoclonal antibody is administered before the first therapeutic antibody.

5. The method of claim 2, wherein the second therapeutic antibody is administered concurrently with the first therapeutic antibody.

6. The method of claim 2, wherein the dysregulated lymphatic system is further characterized by one or more conditions chosen from abnormal lymphatic development, lymphatic proliferation, lymphangiogenesis, impaired lymphatic vessel function, dysregulated lymphatic vessel function, augmented tumor cell lymphatic infiltration, lymphangitic carcinomatosis, abnormal functioning or homeostatic regulation, lymphatic remodeling, physical pressure upon lymphatics, altered tumoral lymphatic development, altered tumoral lymphangiogenesis, and output blockage of lymphatic structures in lymphatic organs.

7. The method of claim 2, wherein the cancer is chosen form lung cancer, breast cancer, a cancer of the gastrointestinal tract, a cancer of unknown origin, head and neck cancer, bladder cancer, prostate cancer, skin cancer, kidney cancer, a primary brain tumor, ocular tumor, sarcoma, a cancer of primary soft tissue, mesenchymal cancer, bone cancer, a tumor of the lymphatic system, and leukemia.

8. The method of claim 7, wherein the cancer is lung cancer, and the method further comprises administering one or more drugs chosen from afatinib dimaleate, alectinib, bevacizumab, carboplatin, ceritinib, crizotinib, docetaxel, doxorubicin, erlotinib, etoposide, everolimus, gefitinib, gemcitabine, mechlorethamine, methotrexate, necitumumab, nivolumab, osimertinib, paclitaxel, paclitaxel albumin-stabilized nanoparticles, pembrolizumab, pemetrexed, ramucirumab, topotecan, vinorelbine, pharmaceutically acceptable salts thereof, and combinations thereof.

* * * * *